United States Patent
Akerele-Ale et al.

(10) Patent No.: US 12,011,552 B2
(45) Date of Patent: Jun. 18, 2024

(54) DUAL-STAGE SYRINGES FOR INDEPENDENT DELIVERY OF TWO OR MORE FLUIDS

(71) Applicant: Bard Peripheral Vascular, Inc., Tempe, AZ (US)

(72) Inventors: Oladipo Peter Akerele-Ale, Tempe, AZ (US); Casey Tyler Hebert, Tempe, AZ (US); Amanda Kingman, Phoenix, AZ (US); Alex Palmer, Scottsdale, AZ (US); Bill Parmentier, Franklin Lakes, NJ (US); Brandon David Simmons, Tempe, AZ (US); Mark Nicholas Wright, Gilbert, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 884 days.

(21) Appl. No.: 17/056,034

(22) PCT Filed: May 17, 2019

(86) PCT No.: PCT/US2019/032983
§ 371 (c)(1),
(2) Date: Nov. 17, 2020

(87) PCT Pub. No.: WO2019/222699
PCT Pub. Date: Nov. 21, 2019

(65) Prior Publication Data
US 2021/0213301 A1    Jul. 15, 2021

Related U.S. Application Data

(60) Provisional application No. 62/673,628, filed on May 18, 2018, provisional application No. 62/673,632, filed on May 18, 2018.

(51) Int. Cl.
*A61M 25/01* (2006.01)
*A61K 51/12* (2006.01)
(Continued)

(52) U.S. Cl.
CPC ..... *A61M 25/0147* (2013.01); *A61K 51/1241* (2013.01); *A61M 5/1785* (2013.01);
(Continued)

(58) Field of Classification Search
CPC .. A61M 25/0147; A61M 5/1785; A61M 5/19; A61M 5/3129; A61M 5/31571;
(Continued)

(56) References Cited

U.S. PATENT DOCUMENTS

| | | |
|---|---|---|
| 4,313,440 A | 2/1982 | Ashley |
| 4,367,738 A | 1/1983 | Legendre |

(Continued)

FOREIGN PATENT DOCUMENTS

| | | |
|---|---|---|
| CN | 101360527 A | 2/2009 |
| DE | 3035290 A1 | 4/1982 |

(Continued)

OTHER PUBLICATIONS

Chiesa, C. et al.; A dosimetric treatment planning strategy in radioembolization of hepatocarcinoma with 90Y glass microspheres; The Quarterly Journal of Nuclear Medicine and Molecular Imaging, vol. 56, No. 6; Dec. 1, 2012.

(Continued)

*Primary Examiner* — Sunita Reddy
(74) *Attorney, Agent, or Firm* — Dinsmore & Shohl LLP

(57) ABSTRACT

In the present disclosure, embodiments of dual-stage syringes are disclosed along with delivery systems incorporating the dual-stage syringes. Embodiments of the dual-stage syringes described herein include sleeved dual-stage (Continued)

syringes, turn-key dual-stage syringes and dual-stage syringes including one or more one-way valves.

11 Claims, 41 Drawing Sheets

(51) Int. Cl.
    *A61M 5/178*     (2006.01)
    *A61M 5/19*     (2006.01)
    *A61M 5/31*     (2006.01)
    *A61M 5/315*     (2006.01)
    *A61M 25/00*     (2006.01)
    *A61M 25/09*     (2006.01)
    *A61N 5/10*     (2006.01)
    *G16H 20/17*     (2018.01)

(52) U.S. Cl.
    CPC ............ *A61M 5/19* (2013.01); *A61M 5/3129* (2013.01); *A61M 5/31571* (2013.01); *A61M 25/0021* (2013.01); *A61M 25/09* (2013.01); *A61N 5/1002* (2013.01); *A61N 5/1007* (2013.01); *G16H 20/17* (2018.01); *A61M 2025/0042* (2013.01); *A61M 2025/09075* (2013.01); *A61M 2025/09166* (2013.01); *A61M 2205/14* (2013.01); *A61M 2205/3331* (2013.01); *A61M 2205/3334* (2013.01); *A61M 2205/50* (2013.01); *A61M 2206/11* (2013.01); *A61N 2005/1019* (2013.01)

(58) Field of Classification Search
    CPC .............. A61M 25/0021; A61M 25/09; A61M 2025/0042; A61M 2025/09075; A61M 2025/09166; A61M 2205/14; A61M 2205/3331; A61M 2205/3334; A61M 2205/50; A61M 2206/11; A61M 5/204; A61M 5/1409; A61M 5/14216; A61M 5/1456; A61M 5/16809; A61M 2005/1787; A61M 2005/2414; A61M 2005/247; A61M 2005/31598; A61M 2025/0004; A61M 2025/0031; A61M 2025/0036; A61M 2025/004; A61M 2025/0073; A61M 2025/0076; A61M 2025/0081; A61M 2025/0681; A61M 2202/0007; A61M 2205/32; A61M 2205/3306; A61M 2205/3317; A61M 2205/502; A61M 5/14566; A61M 2039/1027; A61M 2039/1072; A61M 2205/3327; A61M 39/10; A61M 2039/1033; A61M 2205/505; A61M 2205/8206; A61M 5/2448; A61M 25/0012; A61M 25/003; A61M 25/0071; A61M 25/008; A61M 25/0082; A61M 25/0108; A61M 39/1011; A61K 51/1241; A61K 51/1251; A61K 51/1244; A61K 51/1255; A61N 5/1002; A61N 5/1007; A61N 2005/1019; A61N 5/1001; A61N 2005/1074; A61N 2005/1089; G10H 20/17; G10H 40/63
    USPC ........................................................ 600/1–8
    See application file for complete search history.

(56) References Cited

U.S. PATENT DOCUMENTS

| | | | |
|---|---|---|---|
| 5,478,323 A | 12/1995 | Westwood et al. | |
| 5,496,284 A | 3/1996 | Waldenburg | |
| 6,093,170 A * | 7/2000 | Hsu | A61M 5/3271 604/218 |
| 6,152,913 A | 11/2000 | Feith et al. | |
| 6,508,807 B1 | 1/2003 | Peters | |
| 6,606,370 B1 | 8/2003 | Kasprowicz | |
| 6,669,671 B1 * | 12/2003 | Mohammad | A61M 5/3232 604/196 |
| 6,723,074 B1 | 4/2004 | Halseth | |
| 7,713,239 B2 | 5/2010 | Uber, III et al. | |
| 2001/0021826 A1 | 9/2001 | Winkler | |
| 2003/0201639 A1 | 10/2003 | Korkor | |
| 2004/0111078 A1 | 6/2004 | Miyahara | |
| 2004/0258614 A1 | 12/2004 | Line et al. | |
| 2005/0085685 A1 | 4/2005 | Barbut | |
| 2005/0267411 A1 * | 12/2005 | Chen | A61M 5/50 604/110 |
| 2006/0033334 A1 | 2/2006 | Weber et al. | |
| 2006/0091329 A1 | 5/2006 | Eguchi | |
| 2006/0258977 A1 * | 11/2006 | Lee | A61M 5/31596 604/82 |
| 2006/0293552 A1 | 12/2006 | Polsinelli et al. | |
| 2007/0129591 A1 | 6/2007 | Yanke et al. | |
| 2007/0141339 A1 | 6/2007 | Song et al. | |
| 2008/0058719 A1 | 3/2008 | Edwards et al. | |
| 2008/0103564 A1 | 5/2008 | Burkinshaw et al. | |
| 2008/0200747 A1 | 8/2008 | Wagner et al. | |
| 2008/0281266 A1 | 11/2008 | Walton | |
| 2009/0018498 A1 | 1/2009 | Chiu et al. | |
| 2009/0092677 A1 | 4/2009 | Richard | |
| 2009/0232586 A1 | 9/2009 | Diodati et al. | |
| 2010/0084585 A1 | 4/2010 | Prosser | |
| 2010/0100033 A1 * | 4/2010 | Fojtik | A61M 3/0233 604/35 |
| 2012/0190976 A1 | 7/2012 | Kleinstreuer | |
| 2012/0201726 A1 | 8/2012 | Pearcy et al. | |
| 2013/0165899 A1 | 6/2013 | Haueter et al. | |
| 2013/0317277 A1 | 11/2013 | Lemer | |
| 2014/0046295 A1 | 2/2014 | Uber, III et al. | |
| 2014/0163302 A1 | 6/2014 | Fox et al. | |
| 2014/0207178 A1 | 7/2014 | Chomas et al. | |
| 2014/0236093 A1 | 8/2014 | Eggert et al. | |
| 2014/0257233 A1 | 9/2014 | Cowan | |
| 2014/0276039 A1 * | 9/2014 | Cowan | A61M 5/31513 600/432 |
| 2015/0273089 A1 | 10/2015 | Gray | |
| 2015/0285282 A1 | 10/2015 | Weitz et al. | |
| 2016/0325047 A1 | 11/2016 | Vedrine et al. | |
| 2016/0331853 A1 | 11/2016 | Taub | |
| 2016/0331998 A1 | 11/2016 | Hoffman et al. | |
| 2017/0065732 A1 | 3/2017 | Srinivas et al. | |
| 2017/0120032 A1 | 5/2017 | Miyazaki et al. | |
| 2017/0151357 A1 | 6/2017 | Cade | |
| 2017/0189569 A1 | 7/2017 | Souresrafil et al. | |
| 2017/0238951 A1 | 8/2017 | Yang et al. | |
| 2017/0304151 A1 | 10/2017 | Van Den Berg et al. | |
| 2020/0129695 A1 * | 4/2020 | Brandeis | A61M 5/31581 |

FOREIGN PATENT DOCUMENTS

| | | |
|---|---|---|
| DE | 4318101 A1 | 12/1994 |
| EP | 2179758 A2 | 4/2010 |
| FR | 2917981 A1 | 1/2009 |
| JP | 2006017660 A | 1/2006 |
| JP | 2014525799 A | 10/2014 |
| JP | 2015523867 A | 8/2015 |
| WO | 2007008511 A2 | 1/2007 |
| WO | 2009039203 A2 | 3/2009 |
| WO | 2011014562 A1 | 2/2011 |
| WO | 2012006555 A1 | 1/2012 |
| WO | 2012118687 A1 | 9/2012 |
| WO | 2013153722 A1 | 10/2013 |
| WO | 2014165058 A1 | 10/2014 |
| WO | 2016049685 A1 | 4/2016 |
| WO | 2016161346 A1 | 10/2016 |
| WO | 2017053398 A1 | 3/2017 |
| WO | 2017157974 A1 | 9/2017 |
| WO | 2019006099 A1 | 1/2019 |

(56) References Cited

FOREIGN PATENT DOCUMENTS

| WO | 2019222680 A1 | 11/2019 |
|---|---|---|
| WO | 2019222700 A1 | 11/2019 |
| WO | 2019222713 A1 | 11/2019 |

OTHER PUBLICATIONS

Chiesa, C. et al.; Radioembolization of hepatocarcinoma with 90Y glass microspheres: development of an individualized treatment planning strategy based on dosimetry and radiobiology; European Journal of Nuclear Medicine and Molecular Imaging, Springer Verlag, Heidelberg, DE; vol. 42; No. 11; Jun. 27, 2015.
Spreafico, C. et al.; The dosimetric importance of the No. of 90Y microspheres in liver transarterial radioembolizaiton (TARE); European Journal of Nuclear Medicine and Molecular Imaging, Springer Verlag, Heidelberg, DE; vol. 41, No. 4; Jan. 30, 2014.
International Search Report and Written Opinion dated Aug. 1, 2019 pertaining to International Application No. PCT/US2019/032983.
International Search Report and Written Opinion dated Dec. 13, 2019 pertaining to International Application No. PCT/US2019/032987.
International Search Report and Written Opinion dated Oct. 16, 2019 pertaining to International Application No. PCT/US2019/032955.
International Search Report and Written Opinion dated Jul. 23, 2019 pertaining to International Application No. PCT/US2019/032950.
International Search Report and Written Opinion dated Sep. 24, 2019 pertaining to International Application No. PCT/US2019/033011.
International Search Report and Written Opinion dated Jul. 26, 2019 pertaining to International Application No. PCT/US2019/032965.
International Search Report and Written Opinion dated Jul. 29, 2019 pertaining to International Application No. PCT/US2019/032954.
International Search Report and Written Opinion dated Aug. 7, 2019 pertaining to International Application No. PCT/US2019/032986.
Arepally, A.; Quantification and Reduction of Reflux during Embolotherapy Using an Antireflux Catheter and Tantalum Microspheres: Ex Vivo Analysis; J Vasc Interv Radiol; 2013; 24:575-580.
Chung, J. et al.; Novel use of the Surefire antireflux device in subtotal splenic embolization; Journal of Vascular Surgery Cases; Dec. 1, 2015; pp. 242-245; vol. 1, No. 4.
Ho, S. et al; Clinical evaluation of the partition model for estimating radiation doses from yttrium-90 microspheres in the treatment of hepatic cancer; European Journal of Nuclear Medicine, Springer, Berlin, Heidelberg, DE: vol. 24. No. 3; Mar. 1, 1997.
Hospital Clinics et al.; Y-90 MicroSpheres (SIRSpheres) for treatment of hepatocellular carcinoma; Mar. 1, 2017.
Morshedi, M. et al.; Yttrium-90 Resin Microsphere Radioembolization Using an Antireflux Catheter: An Alternative to Traditional Coil Embolization for Nontarget Protection; Cardiovasc Intervent Radiol; 2015; 38:381-38; Springer.
Sirtex Medical Limited: Sirtex Medical Products Pty Ltd SIR-Spheres (Ytttrium-90 Microspheres); Apr. 1, 2005.
Theragenics Corp.; Therasphere IDOC TM; Aug. 4, 2015.
Tong, A. et al; Yttrium-90 hepatic radioembolization: clinical review and current techniques in interventional radiology and personalized dosimetry; British Journal of Radiology; vol. 89, No. 1062; Jun. 1, 2016.
US FDA; Theresphere IDOC—Humanitarian Device Exemption (HDE); Sep. 14, 2015.
Westcott, M. et al.; The development, commercialization, and clinical context of yttrium-90 radiolabeled resin and glass microspheres; Advances in Radiation Oncology; 2016; vol. 1; pp. 351-364.
Sirtex Medical Limited; SMAC-SIR-Spheres Microspheres Activity Calculator; May 6, 2018.
Office Action dated Mar. 14, 2023 pertaining to JP application No. 2020-564538.
Chinese Office Action dated Dec. 11, 2023 pertaining to CN application 201980046620.X.

\* cited by examiner

DUAL-STAGE SYRINGES FOR INDEPENDENT DELIVERY OF TWO OR MORE FLUIDS

CROSS-REFERENCE TO RELATED APPLICATIONS

This application is a National Stage Entry under 35 U.S.C. § 371 of International Patent Application No. PCT/US2019/032983, entitled "DUAL-STAGE SYRINGES FOR INDEPENDENT DELIVERY OF TWO OR MORE FLUIDS", filed May 17, 2019, which claims the benefit of priority to U.S. Provisional App. No. 62/673,632, entitled "RADIOEMBOLIZATION DELIVERY DEVICE" filed May 18, 2018, the disclosure of which is incorporated by reference herein; and to U.S. Provisional App. No. 62/673,628, entitled "DUAL-STAGE SYRINGES WITH LOCKING MECHANISM" filed May 18, 2018, the disclosure of which is incorporated by reference herein.

TECHNICAL FIELD

The present disclosure relates generally to syringes and, more particularly, to dual-stage syringes that deliver multiple fluids independently.

BACKGROUND

In cancer treatments involving radiation therapy, inadvertent or excess exposure to radiation from radioactive therapeutic agents can be harmful and potentially lethal to patients or medical personnel. Accordingly, medical instruments for radiation therapies must be configured to localize the delivery of radioactive material to a particular area of the patient's body while shielding others from unnecessarily being exposed to radiation.

Transarterial Radioembolization is a transcatheter intra-arterial procedure performed by interventional radiology and is commonly employed for the treatment of malignant tumors. During this medical procedure, a microcatheter is navigated into a patient's liver, where radioembolizing microspheres loaded with a radioactive compound, such as yttrium-90 ($^{90}Y$ or Y90), are delivered to the targeted tumors. The microspheres embolize blood vessels that supply the tumors while also delivering radiation to kill tumor cells.

Generally, medical devices for performing radioembolization procedures require multiple syringes, external tubing, a vial containing the radioactive compound, and a bulky shield assembly for containing and shielding the radioactive vial. Such devices typically involve time consuming and labor-intensive setup procedures. The complex devices are commonly stationary and thereby limit a physician's mobility in an operating room to within a certain proximity of the device.

Routine manipulation of a product container storing radioactive material during radioembolization procedures generally requires a Nuclear Medicine Technician, who handles the material with forceps or tweezers. This process involves further potential of exposing additional medical personnel to radioactivity, and contaminating the operating room. Syringes for manually administering the radioactive compound are prone to inconsistent flow rates and pressures. Insufficient injection rates result in decreased bead dispersion, which may impact efficacy of the treatment.

SUMMARY

Embodiments of the present disclosure are to be used in any technical setting where it is necessary to deliver two separate and isolated media, such as during Transarterial Radioembolization for the treatment of malignant liver tumors. During a Transarterial Radioembolization procedure, a microcatheter is navigated into the liver, and a therapeutic agent, such as a radiotherapeutic agent included in microspheres, may be delivered to the targeted tumors. Throughout this procedure, different media may be used including saline/D5W, contrast agent, and the microspheres. As a result, a minimum of three different syringes are necessary, resulting in increased setup and operating time. Another issue may arise during Transarterial Radioembolization procedures when using a traditional style syringe, as two or more separate syringes are needed during the device activation. The first syringe may be an empty or prefilled syringe of saline for pumping. During the exchange of two or more independent syringes, there is a risk of air entering the system.

This disclosure describes a dual-stage syringe having two independent reservoirs that are engaged in series via a single plunger for the injection or distribution of two separate media. In embodiments, the dual-stage syringes disclosed herein may be manually driven.

The dual-stage syringes of the present disclosure may include a single plunger mechanism, which is used to actuate both chambers, and the medium in each chamber is delivered independently. The dual-stage syringes of the present disclosure may allow for the internal or proximal chamber to be filled and purged multiple times without actuating the external or distal chamber. Additionally, some embodiments of the dual-stage syringes disclosed herein may include one or more locking mechanisms, which may provide tactile and audible feedback and assurance for when the various media are exchanged.

Embodiments of the present disclosure may also address one or more of the following shortcomings of existing systems: Difficulty in pushing syringes to pressurize liquids to flow through the microcatheter, numerous cumbersome steps that delay the procedure and cause unnecessary radiation exposure (e.g. turing stopcocks, adjusting needle heights, adjusting tubing sets to dislodge trapped spheres, etc.), inability to control bead flow, delivery volume and delivery rate, inability to easily assay the contained Y90 activity as part of quality-assurance steps, inability to split the therapeutic dose easily to allow treatment at different tumor sites, settling of particles or microspheres in containers or tubings due to inability to mix the particles or microspheres spheres and a cumbersome overall size of devices used for Transarterial Radioembolization, which take up valuable room and access in the operating room.

Example embodiments disclosed herein are directed to locking-mechanism dual-stage syringes.

These and other features, aspects, and advantages of the present disclosure will become better understood with reference to the following description and the appended claims.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
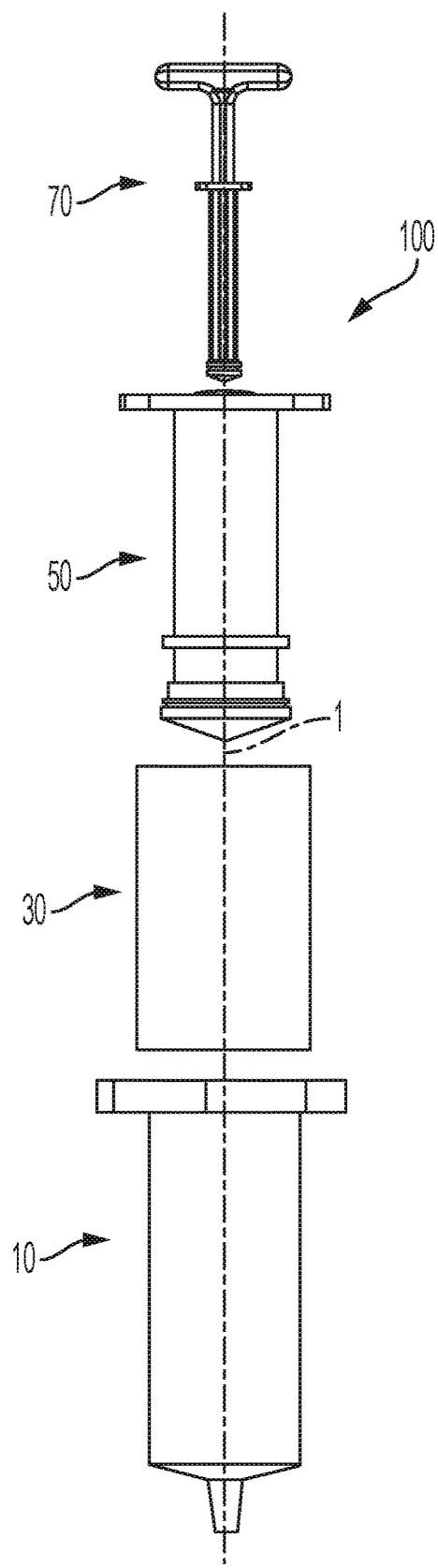
FIG. 1 is a schematic of a dual-stage syringe according to embodiments.

Reference will now be made in detail to embodiments of dual-stage syringes. In particular, embodiments of the dual-stage syringes disclosed herein may be directed to locking-mechanism dual-stage syringes and dual-stage syringes having integrated one-way valves. As will be subsequently described in more detail, embodiments of locking-mechanism dual-stage syringes may include sleeved dual-stage syringes. As will be subsequently described in more detail, other embodiments of locking-mechanism dual-stage syringes may include turn-key dual-stage syringes. In other embodiments of the dual-stage syringes described herein, dual-stage syringes having one or more integrated one-way valves will be subsequently described in more detail.

The dual-stage syringes may be incorporated into any system involving delivering or mixing multiple fluids including medical procedures involving delivery of multiple fluids such as therapeutic agents, flushing solutions, excipient solutions, isotonic sterile solutions, contrast agents, or combinations thereof. In some embodiments, the dual-stage syringes may be incorporated into delivery systems for cancer treatments such as, for example, in delivery systems for chemotherapeutic agents or radiotherapeutic agents. In some embodiments, the dual-stage syringes may be incorporated into delivery systems for chemoembolization therapy or radioembolization therapy, such as for fluids containing radioembolization beads that are mixed with one or more carrier solutions or contrast agents in preparation for being delivered to a patient in need of the therapy. In some embodiments, the dual-stage syringes may be incorporated into delivery systems for transarterial radioembolization for tumor treatments such as, for example, liver-tumor treatments.

As used herein with regard to embodiments of the dual-stage syringes, the relative term "distal" means in the direction toward which a plunger is inserted into a barrel of the dual-stage syringes and in which a fluid is expelled from the dual-stage syringe during operation of the dual-stage syringe. Likewise, the relative term "proximal" means opposite the direction toward which the plunger is inserted into a barrel of the dual-stage syringes and in which the fluid is expelled from the dual-stage syringe during operation of the dual-stage syringe. It should be understood, in general, that directional terms as used herein—for example up, down, right, left, front, back, top, bottom, distal, and proximal—are made only with reference to the figures as drawn and are not intended to imply absolute orientation of any device, of any device component, or of any embodiment as a whole.

Locking-Mechanism Dual-Stage Syringes

Reference will now be made in detail to embodiments of locking-mechanism dual-stage syringes. In embodiments, the locking-mechanism dual-stage syringes may include an external barrel, a primary plunger, and one or more locking mechanisms.

The one or more locking mechanisms may be configured to define a first boundary, a second boundary, and at least three stages. The second boundary may be distal to the first boundary. The at least three stages may include an initial stage, an intermediate stage, and a final stage. In the initial stage, the primary plunger is inserted proximal to the first boundary and may be freely movable distally or proximally. In the intermediate stage, the primary plunger is inserted distal to the first boundary and is prevented from moving proximally beyond the first boundary. In the final stage, the primary plunger is inserted distal to the second boundary and is prevented from moving proximally beyond the second boundary.

In some embodiments, the one or more locking mechanisms may be incorporated into the external barrel, the primary plunger, one or more additional components, or combinations thereof. In further embodiments, the one or more locking mechanisms may be incorporated as a feature on the surface of the external barrel, primary plunger, one or more additional components, or combinations thereof. Such features may be a male feature including one or more nibs, projections, protrusions, or combinations thereof. In embodiments, such features may be a female feature including one or more grooves, tracks, indentations, depressions, other surface modifications, or combinations thereof. In some embodiments, a male feature may have a corresponding female feature. In some embodiments, the one or more locking mechanisms may include a sleeved locking mechanism, a turn-key locking mechanism, or other locking mechanisms.

Referring to FIG. 1, a locking-mechanism dual-stage syringe 100 is provided according to embodiments. In the embodiment exemplified in FIG. 1, the locking-mechanism dual-stage syringe 100 may include an external barrel 10, a primary plunger (piston) 50, that accommodates a secondary plunger 70. In the exploded view of FIG. 1, locking-mechanism dual-stage syringe 100 are depicted as aligned along a longitudinal axis 1 shared by the individual components 10, 50, 70 and the locking-mechanism dual-stage syringe 100 itself, when fully assembled. In embodiments of the locking-mechanism dual-stage syringe 100 fully assembled, particular configurations of which will be described subsequently in greater detail, at least a portion of the primary plunger 50 is accommodated within the external barrel 10, and at least a portion of the secondary plunger may be accommodated within the primary plunger 50. Each of the foregoing individual components 10, 50, 70, the one or more locking mechanisms, and various features thereof, according to embodiments of the locking-mechanism dual-stage syringe 100, will now be described in greater detail.

The locking-mechanism dual-stage syringe 100 may include an external barrel 10. Referring now to FIGS. 1-5, the external barrel 10 may have a primary chamber 90 defined through the external barrel 10 from a proximal opening of the external barrel 10 to a distal opening of the external barrel 10.

In embodiments, the external barrel 10 may be made of various materials such as, for example, polymers, plastics, or metals. Non-limiting example polymers for the external barrel include polycarbonates (PC), polyethylenes (PE), polyethylene terephthalates (PET). Non-limiting example plastics for the external barrel 10 include poly(methyl methacrylate) (PMMA) and composite resins such as polycarbonate loaded with tungsten. Non-limiting example metals and metal alloys for the external barrel 10 include stainless steel, titanium, copper, tungsten, aluminum, pewter, and various alloys of any of these. In some embodiments, the external barrel 10 is made of a radiation shielding material such as the plastics or metals previously listed. The radiation shielding material may have a thickness sufficient to ensure that radiation from a radioactive therapeutic material in the dual-stage syringe having a one or more locking mechanisms cannot penetrate to the environment or cause safety concerns for personnel operating the locking-mechanism dual-stage syringe 100. In embodiments, suitable radiation shielding materials may shield operators of the dual-stage syringe having a sleeved locking mechanism from beta-particle radiation, from x-rays, or both.

Figure 2:
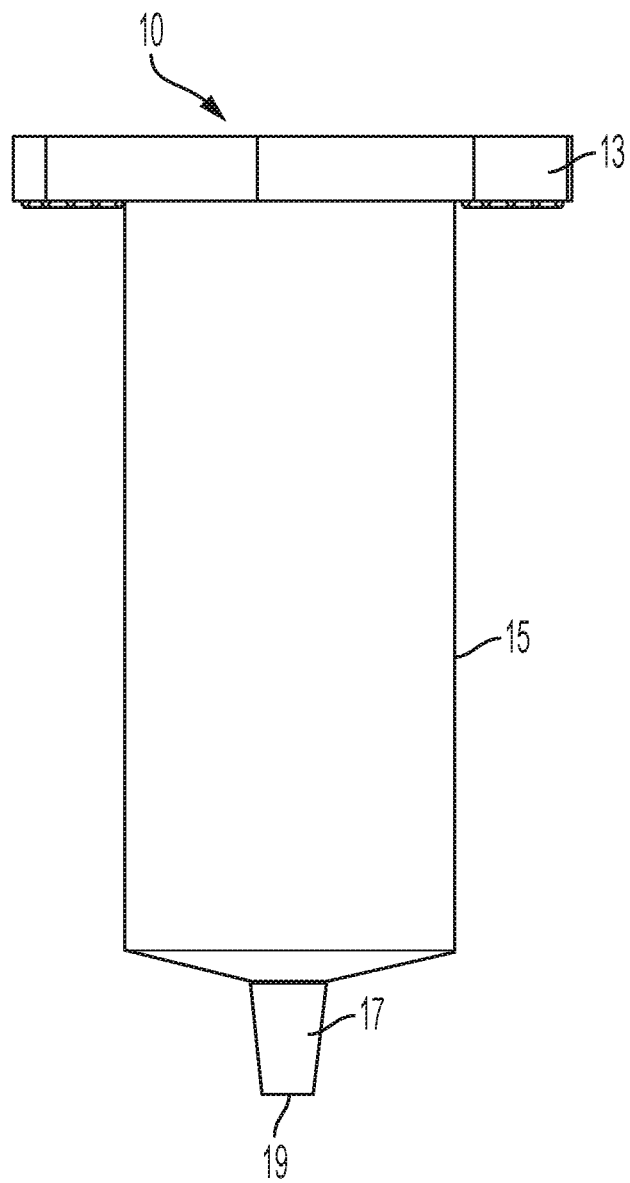
FIG. 2 is a side view of an external barrel of a dual-stage syringe according to embodiments.
Figure 3:
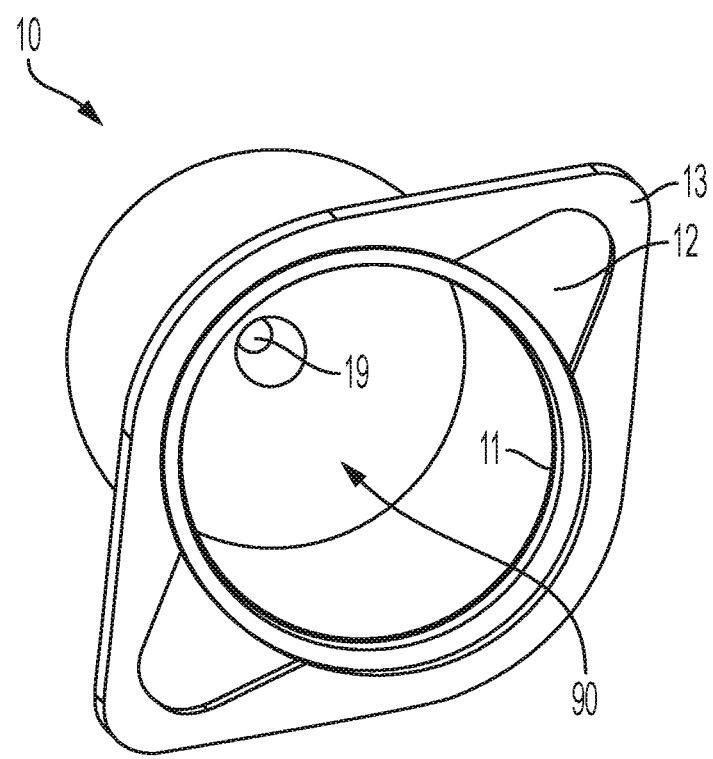
FIG. 3 is a top perspective view of an external barrel of a dual-stage syringe according to embodiments.
Figure 4:
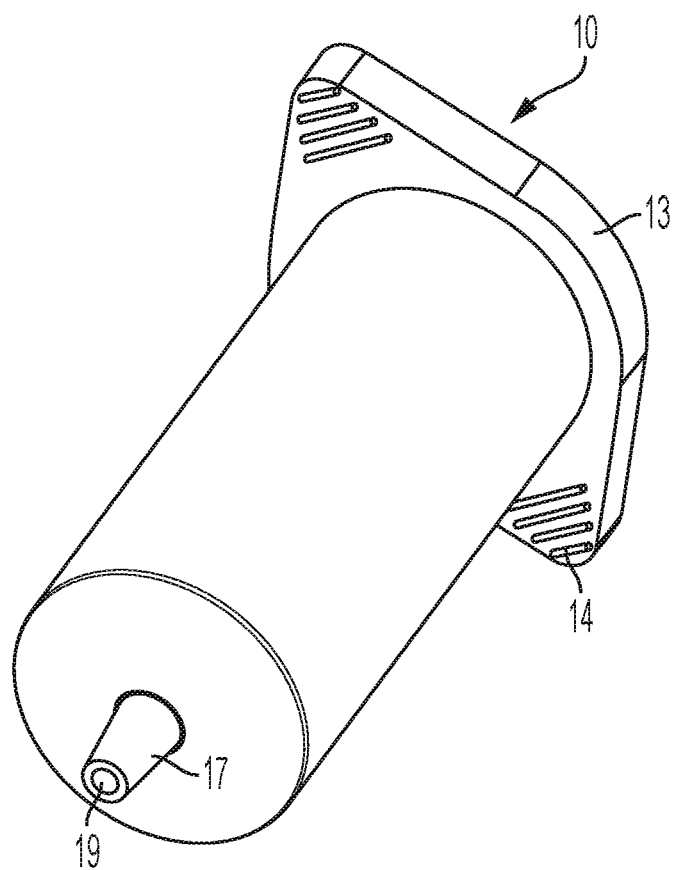
FIG. 4 is a bottom perspective view of an external barrel of a dual-stage syringe according to embodiments.

Referring now to FIGS. 2-4, an exemplary embodiment of the external barrel 10 is provided. In all exemplary embodiments provided in FIGS. 2-4, the external barrel 10 of the locking-mechanism dual-stage syringe 100 may include an external proximal opening 11, a proximal flared edge 13 around the external proximal opening 11, an external distal opening 19 opposite the external proximal opening 11, and a body portion 15 between the proximal flared edge 13 and the external distal opening 19. Referring to FIG. 2, the external barrel 10 may include a neck portion 17 between the body portion 15 and the external distal opening 19.

Referring to FIG. 3, the external barrel 10 may optionally include a proximal depression 12 that may be configured to accommodate corresponding features of the primary plunger 50, as described subsequently in greater detail. The external proximal opening 11 of the external barrel 10 may be sufficiently wide to accommodate the primary plunger 50 through the external proximal opening 11. As will be described subsequently in more detail, in embodiments, the external proximal opening 11 of the external barrel 10 may be sufficiently wide to accommodate a locking mechanism, such as a sleeved locking mechanism, through the external proximal opening 11. Referring still to FIG. 3, the external barrel 10 has a primary chamber 90 defined therein. The primary plunger 50 may be insertable into primary chamber 90. In some embodiments, a locking mechanism may be insertable into primary chamber 90.

Referring to FIG. 4, the external barrel 10 optionally may include gripping features 14 on a distal-facing side of the proximal flared edge 13.

As stated previously, in some embodiments of the locking-mechanism dual-stage syringe 100, the one or more locking mechanisms may be incorporated into the external barrel 10. In such embodiments, the one or more locking mechanisms incorporated into the external barrel 10 as one or more features on the surface of the external barrel 10, such as male features and/or female features. Male features may include, without limitation, nibs, projections, protrusions, or combinations thereof. Female features may include, without limitation, grooves, tracks, indentations, depressions, other surface modifications, and combinations thereof.

In embodiments, the external barrel 10 may include one or more male features on the surface of the external barrel 10. In further embodiments, the one or more male features on the surface of the external barrel 10 may have corresponding one or more female features on the primary plunger 50, one or more additional components, or combinations thereof. In other embodiments, the external barrel 10 may include one or more female features on the surface of the external barrel 10. In further embodiments, the one or more female features on the surface of the external barrel 10 may have a corresponding one or more male features on the primary plunger, one or more additional components, or combinations thereof. In some embodiments, the external barrel 10 may include a combination of male and female features on the surface of the external barrel 10, which may have corresponding female and male features, respectively, on the primary plunger, one or more additional components, or combinations thereof.

Figure 5:
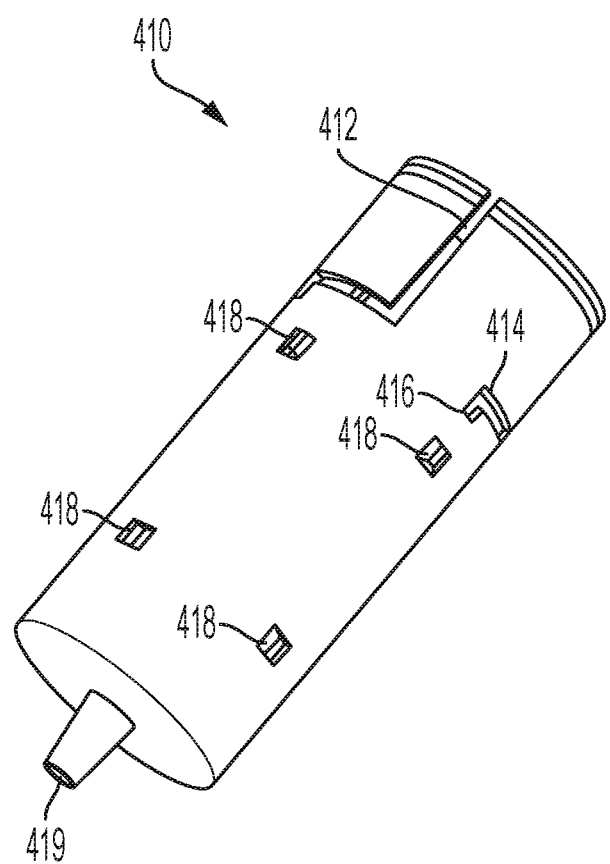
FIG. 5 is a side perspective view of an external barrel of the dual-stage syringe according to embodiments.
Figure 6:
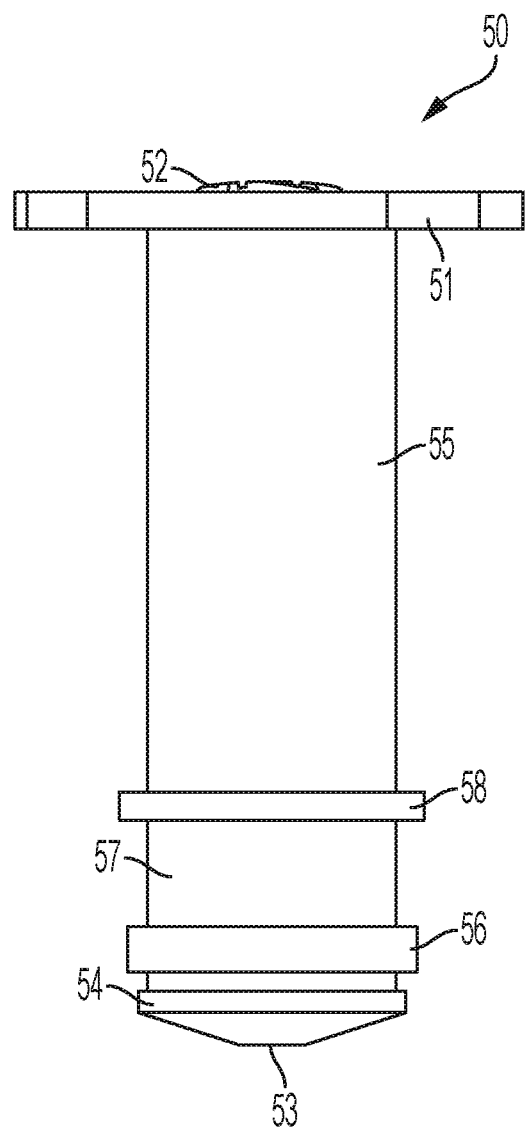
FIG. 6 is a side view of a primary plunger of a dual-stage syringe according to embodiments.
Figure 7:
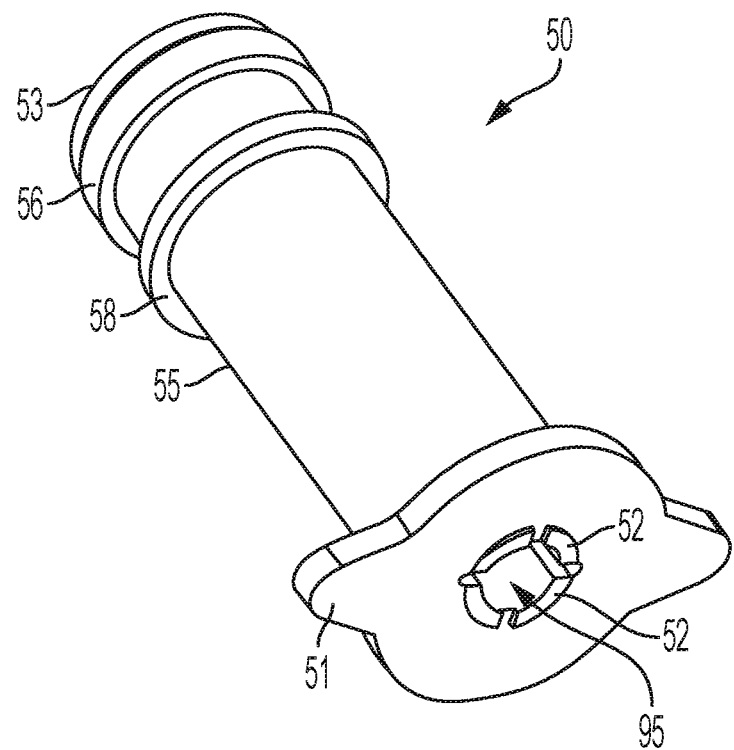
FIG. 7 is a top perspective view of a primary plunger of a dual-stage syringe according to embodiments.

FIG. 5 shows an exemplary embodiment a locking-mechanism dual-stage syringe 100 having one or more locking mechanisms incorporated into the external barrel 410. Referring now to FIG. 5, embodiments of an external barrel 410 may include an initial-stage track 412, an intermediate-stage track 414, and a final-stage track 416 within the external barrel 410. The initial-stage track 412, the intermediate-stage track 414, and the final-stage track 416 are all female features on the surface of external barrel 410. In FIG. 5, indentations 418 are also female features on the surface of external barrel 410. Collectively, the initial-stage track 412, the intermediate-stage track 414, the final-stage track 416, and the indentations 418 may be referred to as the female features of the locking mechanism of the embodiment illustrated in FIG. 5. As will be described subsequently in more detail, the female features of the locking mechanism of the embodiment illustrated in FIG. 5 have corresponding male features on the primary plunger of the embodiment illustrated in FIG. 5. Collectively, the male features and female features of the locking mechanism of the embodiment illustrated in FIG. 5 may be collectively referred to as the turn-key locking mechanism of the embodiment illustrated in FIG. 5. As such, the embodiment illustrated in FIG. 5 may also be referred to as a turn-key embodiment of the locking-mechanism dual-stage syringe 100. In other embodiments, the locking-mechanism dual-stage syringe 100 may include a turn-key locking mechanism that includes only the initial-stage track 412, the intermediate-stage track 414, and the final-stage track 416 but not the indentations 418. In yet other embodiments, the locking-mechanism dual-stage syringe 100 may include a turn-key locking mechanism that includes the initial-stage track 412, the intermediate-stage track 414, the final-stage track 416, the indentations 418, and one or more additional locking mechanisms.

Referring still to FIG. 5, the intersection of the initial-stage track 412 with the intermediate-stage track 414 corresponds to an initial stage of the primary plunger. In the initial stage, the primary plunger is inserted proximal to the initial-stage track 412 and may be freely movable distally or proximally. The intermediate-stage track 414 corresponds to an intermediate stage of the primary plunger. In the intermediate stage, the primary plunger may traverse the intermediate-stage track and is prevented from moving proximally beyond the intermediate-stage track. The intersection of the final-stage track 416 with the intermediate-stage track 414 corresponds to a final stage of the primary plunger. In the final stage, the primary plunger is inserted distal to the intermediate-stage track and is prevented from moving proximally beyond a distal end of the final-stage track. In other embodiments, the locking-mechanism dual-stage syringe 100 may include a turn-key locking mechanism that includes one or more additional tracks in the surface of the external barrel 410, which may define one or more additional stages.

Like other embodiments of the external barrel 10, the external barrel 410 may include any of the polymers, plastics, metals, or alloys listed previously, or it may include other materials, such as nylon.

Reference will now be made to embodiments of the primary plunger 50 of the locking-mechanism dual-stage syringe 100. Referring back to FIG. 1, the primary plunger 50 may have a secondary chamber defined through the primary plunger 50 from a proximal opening of the primary plunger 50 to a sealed distal end of the primary plunger 50, the primary plunger 50 configured to receive a secondary plunger (piston) 70 through the proximal opening of the primary plunger 50. In embodiments, the primary plunger 50 may be sufficiently narrow to be accommodated by external barrel 10.

In embodiments, the primary plunger 50 may be made of various materials such as, for example, polymers, plastics, or metals. Non-limiting example polymers for the external barrel include polycarbonates (PC), polyethylenes (PE), polyethylene terephthalates (PET). Non-limiting example plastics for the primary plunger 50 include poly(methyl methacrylate) (PMMA) and composite resins such as polycarbonate loaded with tungsten. Non-limiting example metals and metal alloys for the primary plunger 50 include stainless steel, lead, copper, tungsten, aluminum, pewter, and various alloys of any of these. In some embodiments, the primary plunger 50 is made of a radiation shielding material such as the plastics or metals previously listed. The radiation shielding material may have a thickness sufficient to ensure that radiation from a radioactive therapeutic material in the dual-stage syringe having a one or more locking mechanisms 100 cannot penetrate to the environment or cause safety concerns for personnel operating the locking-mechanism dual-stage syringe 100. In embodiments, suitable radiation shielding materials may shield operators of the dual-stage syringe having a sleeved locking mechanism from beta-particle radiation, from x-rays, or both.

Referring now to FIGS. 6-9, an exemplary embodiment of the primary plunger 50 is provided. In FIGS. 6-9, the primary plunger 50 may include a proximal wing portion 51, a distal plunger opening 53, and a plunger body portion 55. The primary plunger may include a secondary chamber 95 defined therein from the proximal wing portion 51 to the distal plunger opening 53. The primary plunger 50 optionally may include handle-locking features 52 on the proximal wing portion 51. The secondary chamber 95 may accommodate the secondary plunger 70, which will be described subsequently in more detail. The plunger body portion 55 may include one or more stop rings such as a distal stop ring 56 and a proximal stop ring 58. In some embodiments, both the distal stop ring 56 and the proximal stop ring 58 may be configured to interact with embodiments of a locking mechanism, subsequently described in more detail, as the primary plunger 50 is moved.

Figure 8:
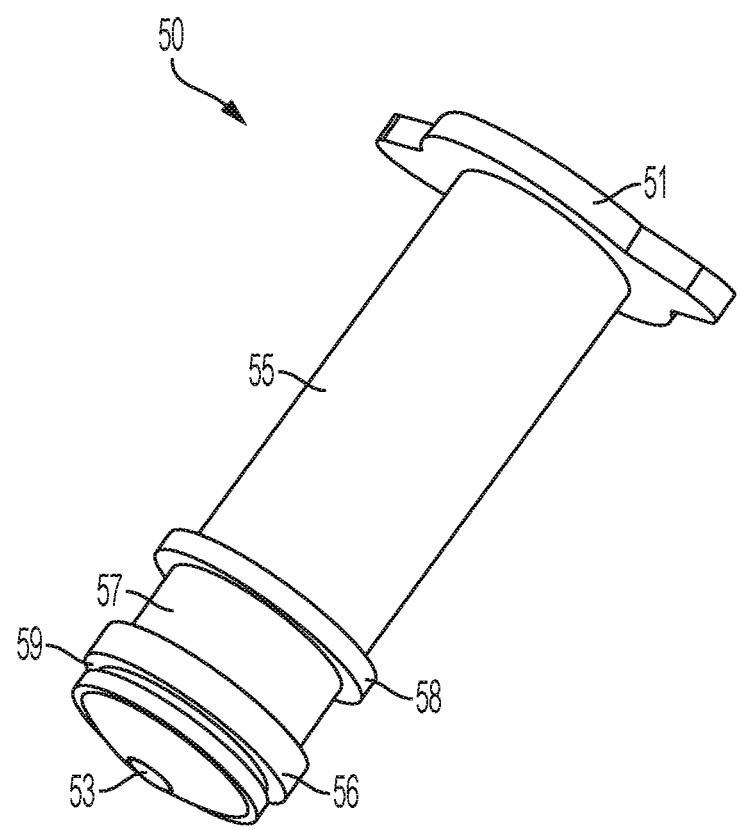
FIG. 8 is a side perspective view of a primary plunger of a dual-stage syringe according to embodiments.
Figure 9:
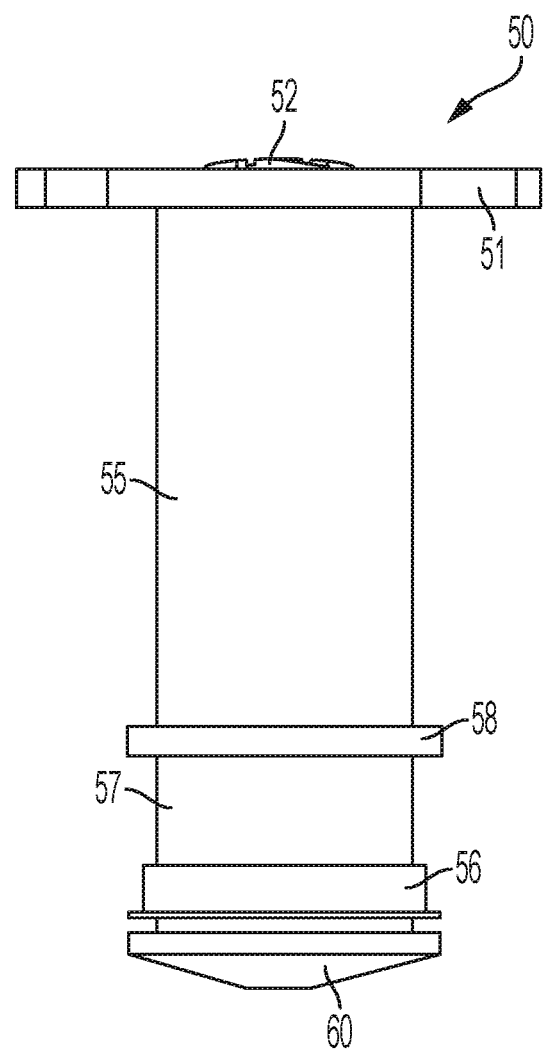
FIG. 9 is a side perspective view of a primary plunger of a dual-stage syringe, including a sealing member on the distal end thereof, according to embodiments.

Referring now to FIGS. 8-9, in embodiments, the primary plunger 50 may include a seal seat 59 for mounting a plunger seal 60. The plunger seal 60 may include one-way valves, flaps, or flow channels. As shown in FIG. 9, in embodiments, the plunger seal 60 may be mounted on the primary plunger, such that the plunger seal 60 covers the distal plunger opening 53 to prevent fluidic flow through the distal plunger opening 53 until an appropriate stage in the operation of the locking-mechanism dual-stage syringe 100, as will be described in greater detail.

In some embodiments of the locking-mechanism dual-stage syringe 100, one or more locking mechanisms may be incorporated into the primary plunger. In such embodiments, the one or more locking mechanisms incorporated into the primary plunger may include one or more features on the surface of the primary plunger, such as male features and/or female features. Male features may include, without limitation, nibs, projections, protrusions, or combinations thereof. Female features may include, without limitation, grooves, tracks, indentations, depressions, other surface modifications, and combinations thereof.

In embodiments, the primary plunger 50 may include one or more male features on the surface of the primary plunger 50. In further embodiments, the one or more male features on the surface of the primary plunger 50 may have corresponding one or more female features on the external barrel, one or more additional components, or combinations thereof. In other embodiments, the primary plunger 50 may include one or more female features on the surface of the primary plunger 50. In further embodiments, the one or more female features on the surface of the primary plunger 50 may have a corresponding one or more male features on the external barrel, one or more additional components, or combinations thereof. In some embodiments, the primary plunger 50 may include a combination of male and female features on the surface of the primary plunger 50, which may have corresponding female and male features, respectively, on the external barrel, one or more additional components, or combinations thereof.

Figure 10:
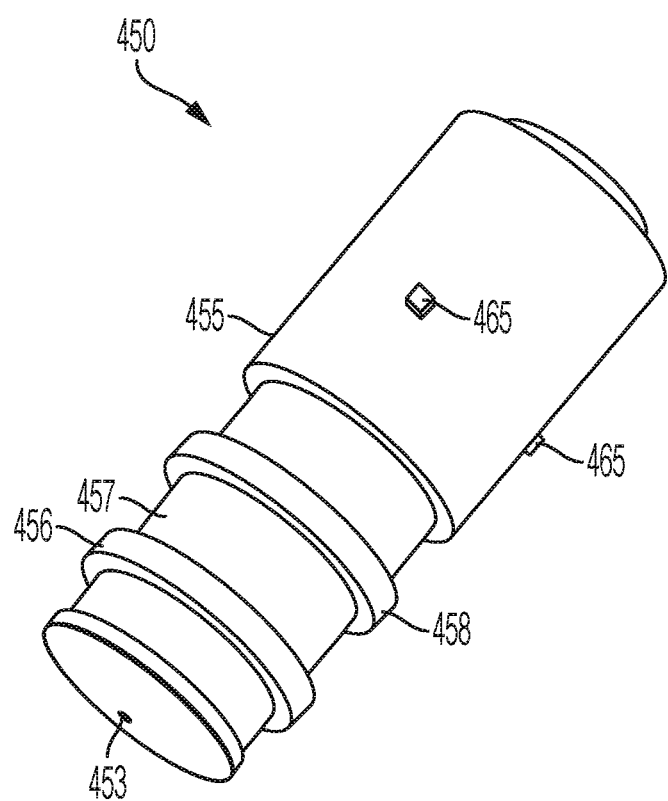
FIG. 10 is a side perspective view of a primary plunger of a dual-stage syringe, including a sealing member on the distal end thereof, according to embodiments.

FIG. 10 shows an exemplary embodiment of a locking-mechanism dual-stage syringe incorporated into the primary plunger. Referring now to FIG. 10, embodiments of a primary plunger 450 includes male features (nibs) 465, which are shaped and sized appropriately to correspond the female features of the turn-key locking mechanism of FIG. 5, previously described. In embodiments male features may be shaped and sized appropriately to travel within the tracks 412, 414, 416 of the external barrel 410

As previously stated, the one or more locking mechanisms of the locking-mechanism dual-stage syringe 100 may be configured to define a first boundary, a second boundary, and at least three stages. The second boundary may be distal to the first boundary. The at least three stages may include an initial stage, an intermediate stage, and a final stage. In the initial stage, the primary plunger is inserted proximal to the first boundary and may be freely movable distally or proximally. In the intermediate stage, the primary plunger is inserted distal to the first boundary and is prevented from moving proximally beyond the first boundary. In the final stage, the primary plunger is inserted distal to the second boundary and is prevented from moving proximally beyond the second boundary.

In some embodiments, the one or more locking mechanisms may be incorporated into a sleeve disposed within the primary chamber 90. For example, the one or more locking mechanisms incorporated into a sleeve disposed within the primary chamber 90 may include a feature on the surface of the sleeve disposed within the primary chamber 90 such as a nib, projection, protrusion, groove, track, indentation, or other surface modification. An example of a locking mechanism incorporated into a sleeve disposed within the primary chamber 90 may include a sleeved locking mechanism, which will now be described in greater detail.

Figure 11:
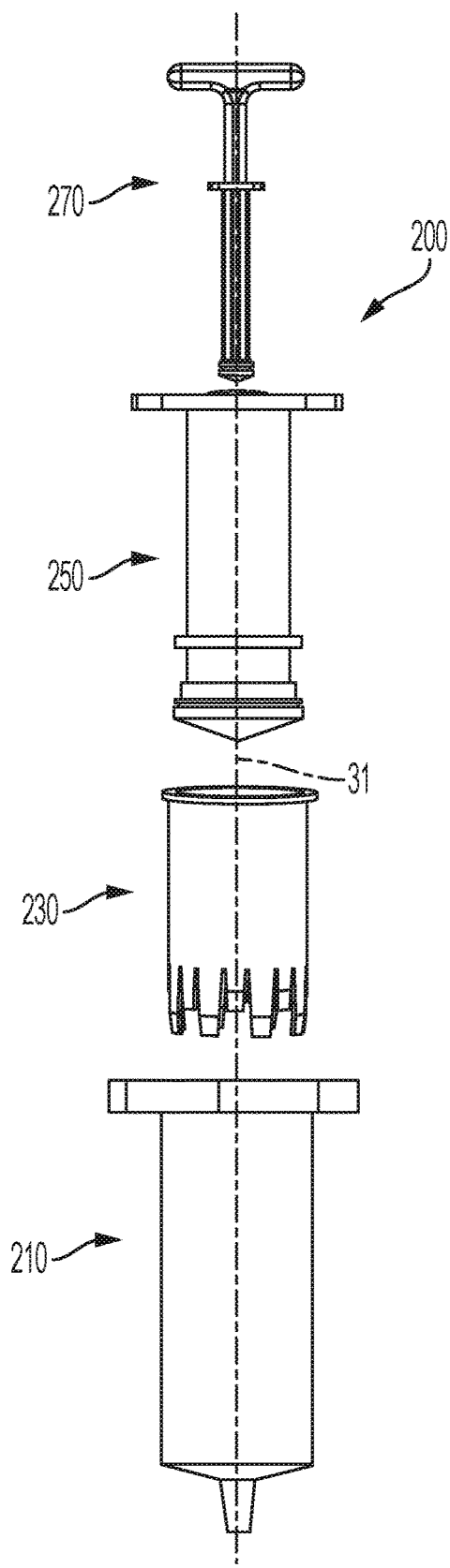
FIG. 11 is an exploded view of a sleeved dual-stage syringe according to embodiments.
Figure 12:
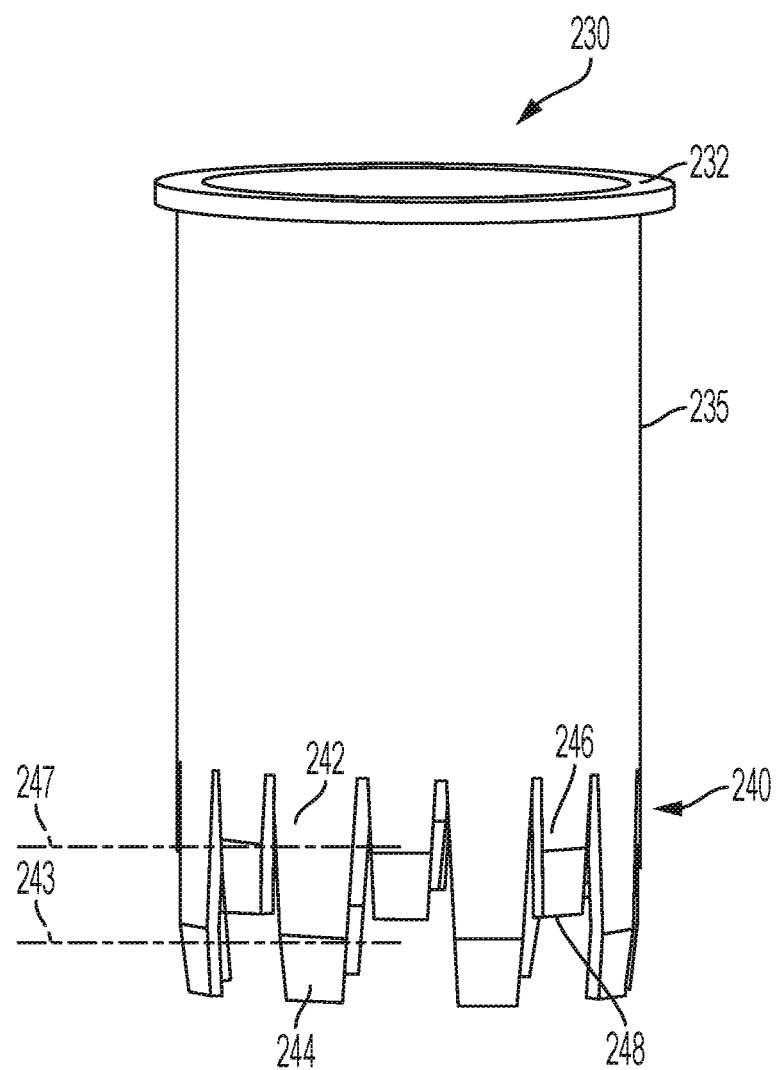
FIG. 12 is a side perspective view of a locking sleeve, according to embodiments.
Figure 13:
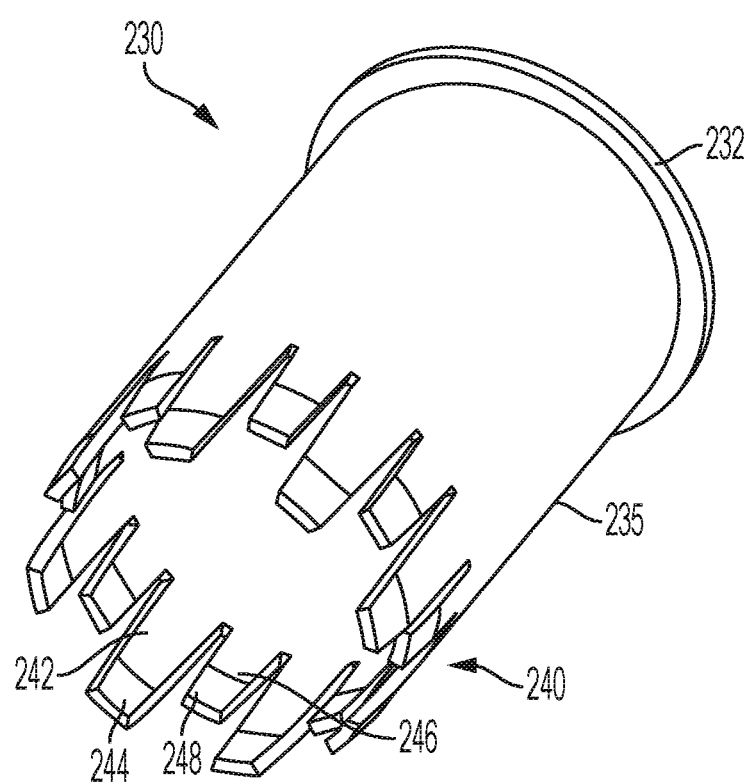
FIG. 13 is a bottom perspective view of the locking sleeve, according to embodiments.
Figure 14:
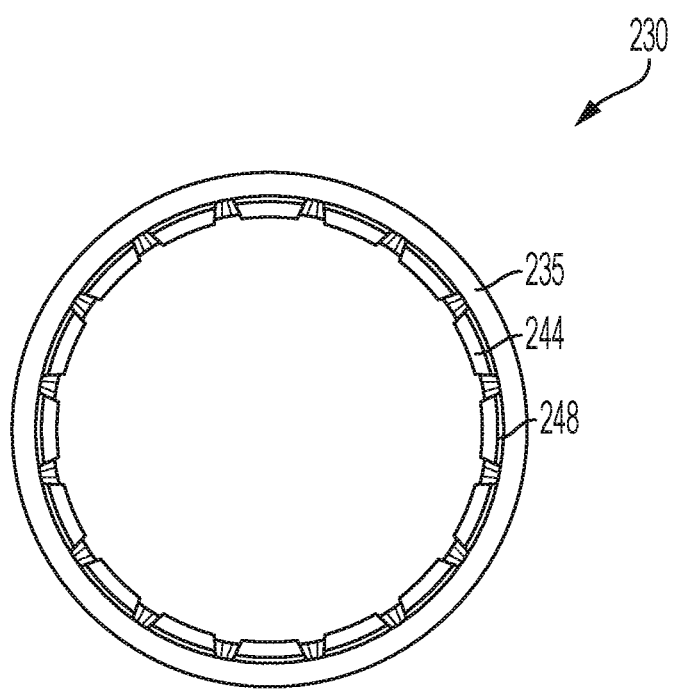
FIG. 14 is a bottom view of the locking mechanism of the locking sleeve, according to embodiments.
Figure 15:
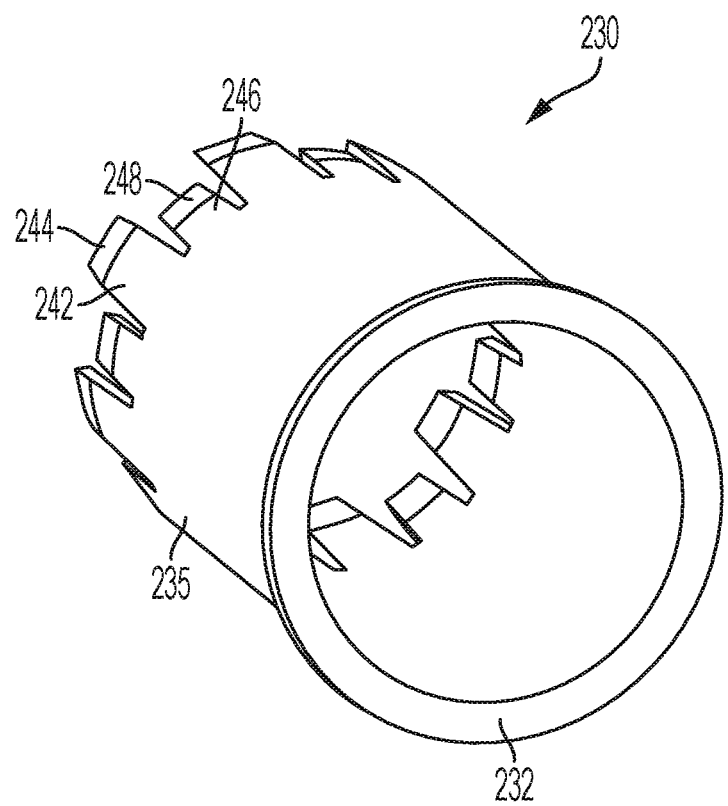
FIG. 15 is a top perspective view of the locking sleeve, according to embodiments.

Embodiments of dual-stage syringes having sleeved locking mechanisms will now be described with reference to FIGS. 11-15. Referring to FIG. 11, a dual-stage syringe having a sleeved locking mechanism 200 according to embodiments may include an external barrel 210, a locking sleeve 230, and a primary plunger 250 that accommodates a secondary plunger 270. In the exploded view of FIG. 11, the components of the dual-stage syringe having a sleeved locking mechanism 300 are depicted as aligned along a longitudinal axis 31 shared by the individual components 210, 230, 250, 270 and the dual-stage syringe having a sleeved locking mechanism 200 itself, when fully assembled. In a dual-stage syringe having a sleeved locking mechanism 200 fully assembled, particular configurations of which will be described subsequently in greater detail, the locking sleeve 230 is accommodated within the external barrel 210, at least a portion of the primary plunger 250 is accommodated within the locking sleeve 230 and the external barrel 210, and at least a portion of the secondary plunger 270 may be accommodated within the primary plunger 250.

Referring again to FIGS. 11-15, embodiments of the dual-stage syringe having a sleeved locking mechanism 200 may include a locking sleeve 230. Referring to FIGS. 11-15, the locking mechanism 230 according to embodiments may include a body portion 235 having a shape conforming to contours of the external barrel 10. The locking mechanism 230 may include one or more features that can be used for integrational assembly, such as a proximal ridge 232 configured to seat the locking mechanism in the external proximal opening 11 of the external barrel 10. The locking mechanism 230 may include distal catch members 240. The distal catch members 240 may have various shapes and dimensions suited to perform a locking function, as will be described subsequently in greater detail. The distal catch members 240 may have sufficient resilience to permit the primary plunger 50 to pass through the locking mechanism in a distal direction, but to deflect outwardly and prevent proximal movement of the primary plunger 50, as will be described.

In the embodiment of FIGS. 11-15, the distal catch members 240 are configured as long catches 242 and short catches 246 alternating around the circumference of the body portion 235 at the distal end of the body portion 235. The long catches 242 include long-catch ends 244 angled slightly inwardly (i.e., toward the longitudinal axis 1 (see FIG. 11)) of the sleeved locking dual-stage syringe 200. The short catches 246 include short-catch ends 248 also angled slightly inwardly. The lengths of the long catches 242 define a distal stop level 243. Likewise, the lengths of the short catches 246 define a proximal stop level 247. As will be described in greater detail subsequently, the distal stop level 243 and the proximal stop level 247, in turn, define positions, beyond which when the primary plunger 50 is inserted into the external barrel 10 and surrounded by the locking mechanism 30, proximal movement of the primary plunger 50 is prevented.

Figure 16:
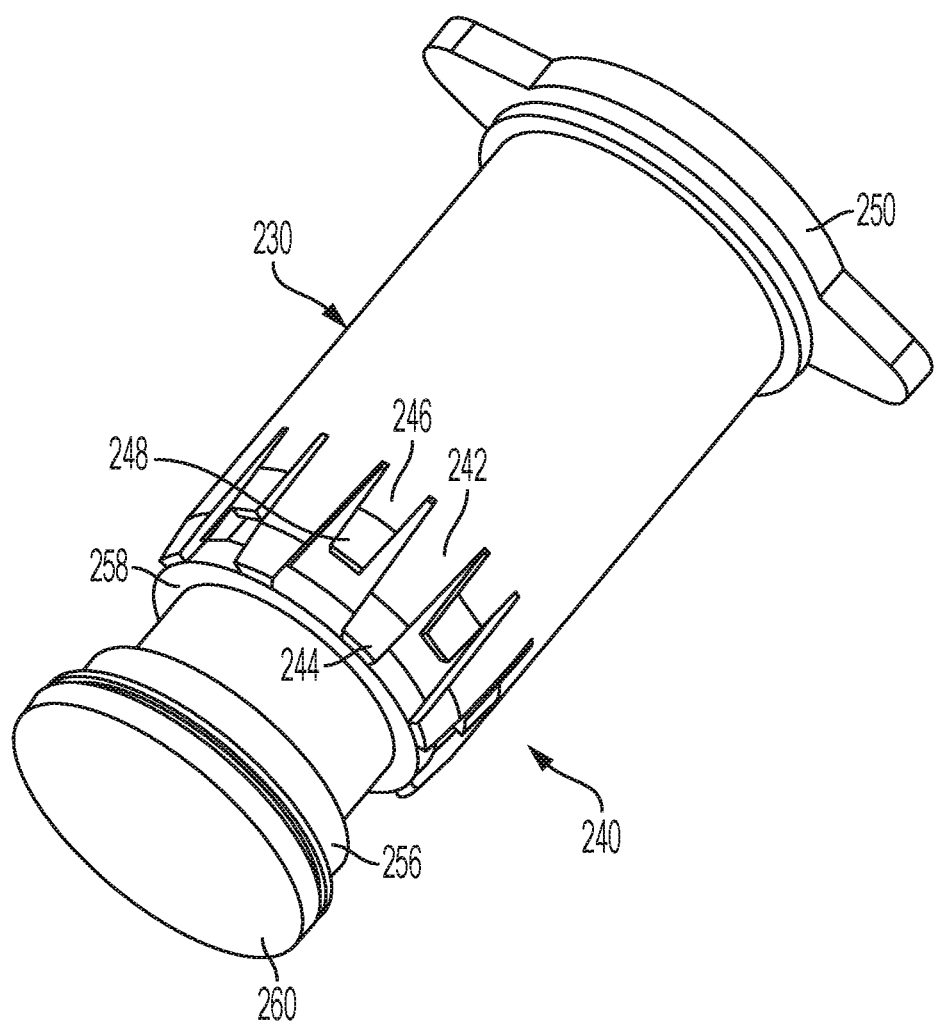
FIG. 16 is a side perspective view of an assembly including the locking mechanism and the primary plunger having a sealing member on the distal end thereof, according to embodiments.
Figure 17:
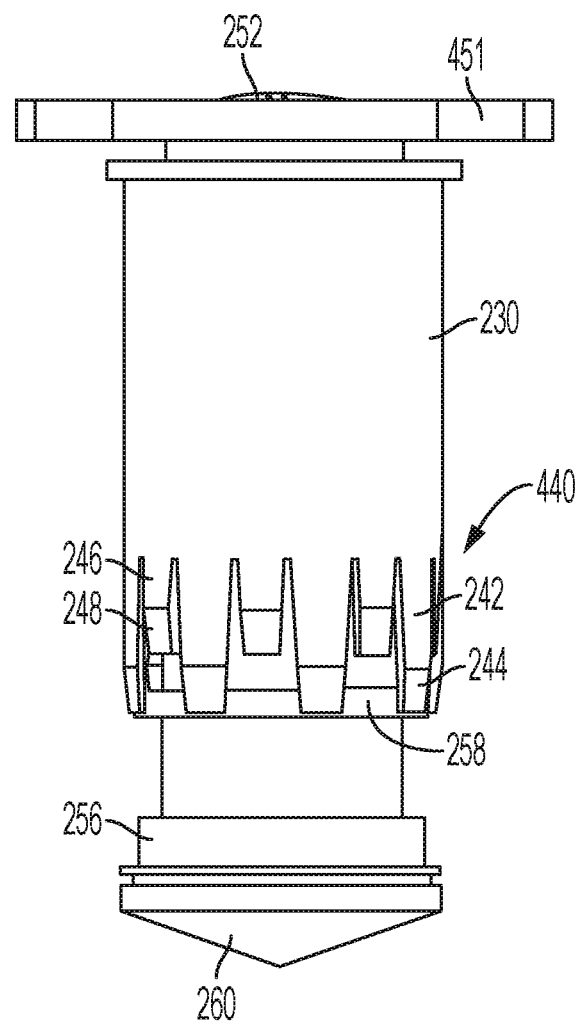
FIG. 17 is a front view of an assembly including the locking mechanism and the primary plunger having a sealing member on the distal end thereof, according to embodiments.

Referring to FIGS. 16-17, the primary plunger 250 is insertable into the locking sleeve 230. As the primary plunger 250 is inserted in the distal direction through the locking sleeve 230, the distal stop ring 256 and, subsequently, the proximal stop ring 258 passes distally beyond the distal catch members 240 (for example, the long catches 342 and the short catches 346). The distal catch members 240 then deflect inwardly, in turn locking the primary plunger 250 in a manner that prevents proximal withdrawal of the primary plunger 250 beyond a point at which the proximal stop ring 358 would pass in a proximal direction back through the distal catch members 240 (i.e., beyond the long-catch ends 44). In other embodiments, the distal catch members 240 may be catches of varying lengths around the circumference of the body portion 235 at the distal end of the body portion 235. In other embodiments, the long catches 242 include long-catch ends 244 that may be angled slightly outwardly (i.e., away from the longitudinal axis 1 (see FIG. 11)) of the sleeved locking dual-stage syringe 200. In further embodiments, the short catches 246 include short-catch ends 248 that may be angled slightly outwardly.

Figure 18:
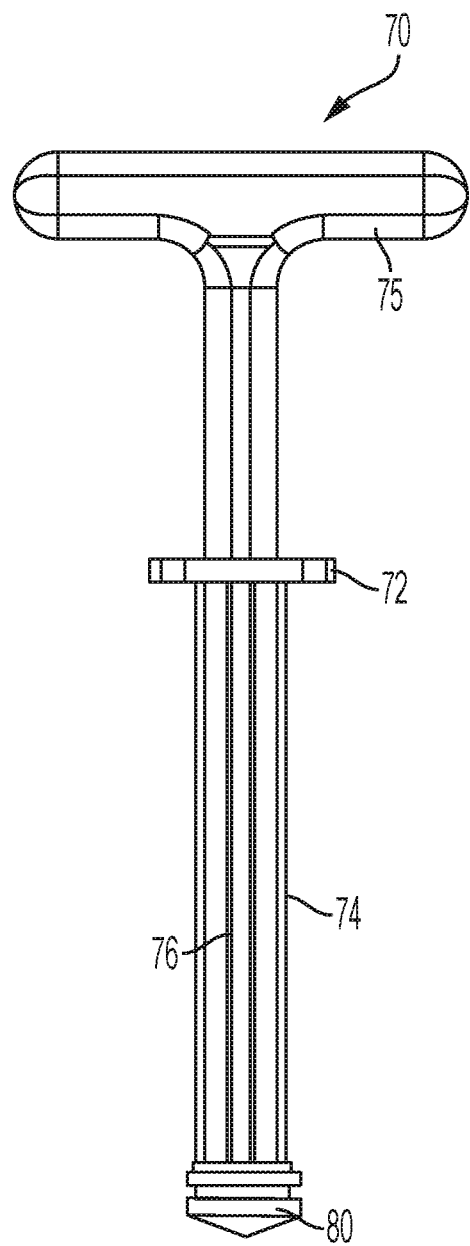
FIG. 18 is a side view of a secondary plunger of a dual-stage syringe, according to embodiments.

Referring to FIG. 18, the secondary plunger 70 may include an elongated portion 74, a handle portion 75, and a secondary seal 80. The elongated portion 74 of the secondary plunger 70 may include ribbed members 76 perpendicular to the elongated portion 74 to provide stability to the elongated portion 74 and facilitate insertion of the secondary plunger 70 into the secondary chamber 95 of the primary plunger 50. The secondary plunger 70 may include an insertion stop 72 that defines a maximum extent to which the secondary plunger 70 may be inserted into the secondary chamber 95 of the primary plunger 50. It should be understood that the insertion stop 72, the elongated portion 74, the handle portion 75, and ribbed members 76 (if any), may have various shapes, sizes, or configurations and are not limited to the specific configuration of FIG. 18.

Figure 28:
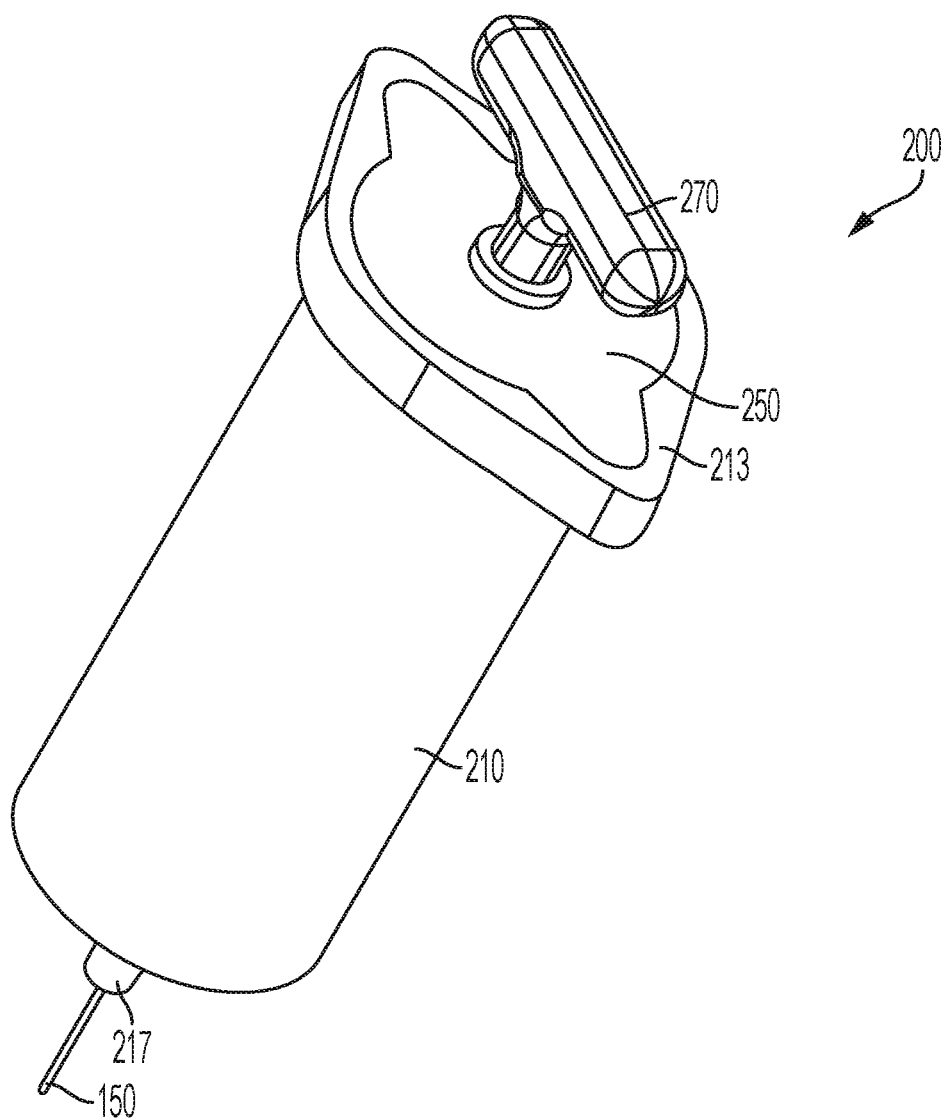
FIG. 28 is a perspective view of a sleeved locking dual-stage syringe according to embodiments, in a delivery configuration.
Figure 29:
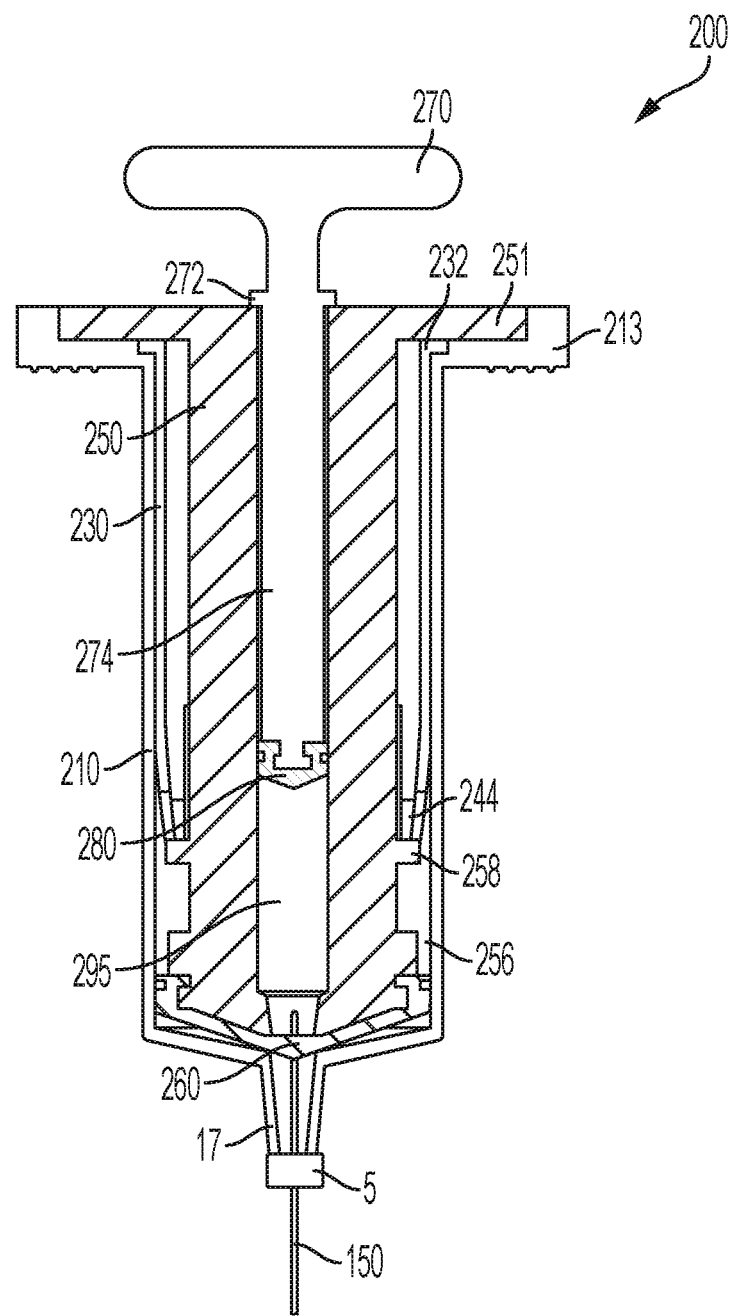
FIG. 29 is a longitudinal cross-section of the sleeved locking dual-stage syringe of FIG. 28 in a delivery configuration.

The primary components of the dual-stage syringes having sleeved locking mechanisms 200 have been described, along with general operating principles of the locking sleeve 230. The primary components and the general operating principles result in at least five operational stages of the dual-stage syringes having sleeved locking mechanisms 200, each of which now will be described with reference to FIGS. 19-29. In particular, the operational stages include a shipped configuration (FIGS. 19-21), a flushed configuration (FIGS. 22-23), a punctured configuration (FIGS. 24-25), a primed configuration (FIGS. 26-27), and a delivery configuration (FIGS. 28-29). It should be understood that description with regard to these operational stages is intended to illustrate one manner of operating the sleeved locking dual-stage syringe 200 and, through illustrating one manner of operating the sleeved locking dual-stage syringe 200, to further elucidate the functions and synergies of the primary components of the sleeved locking dual-stage syringe 200.

Figure 19:
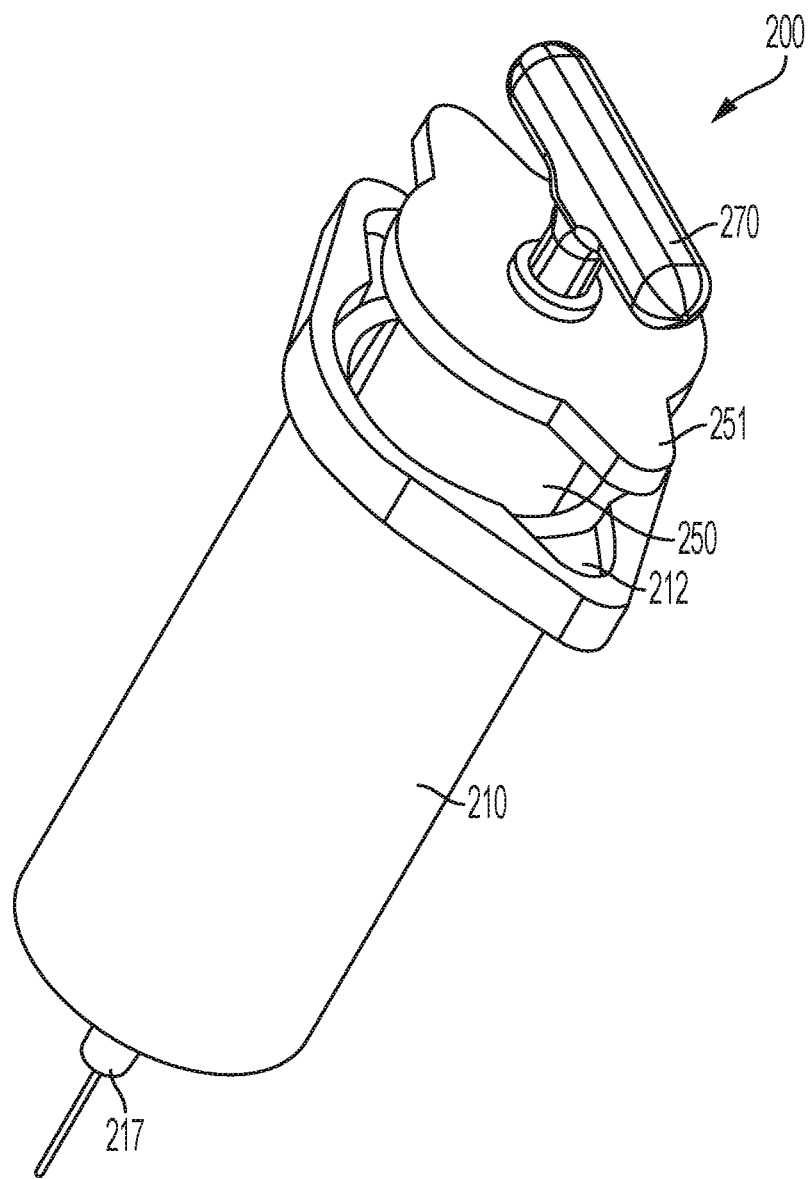
FIG. 19 is a perspective view of a sleeved locking dual-stage syringe according to embodiments, in a shipment configuration.
Figure 20:
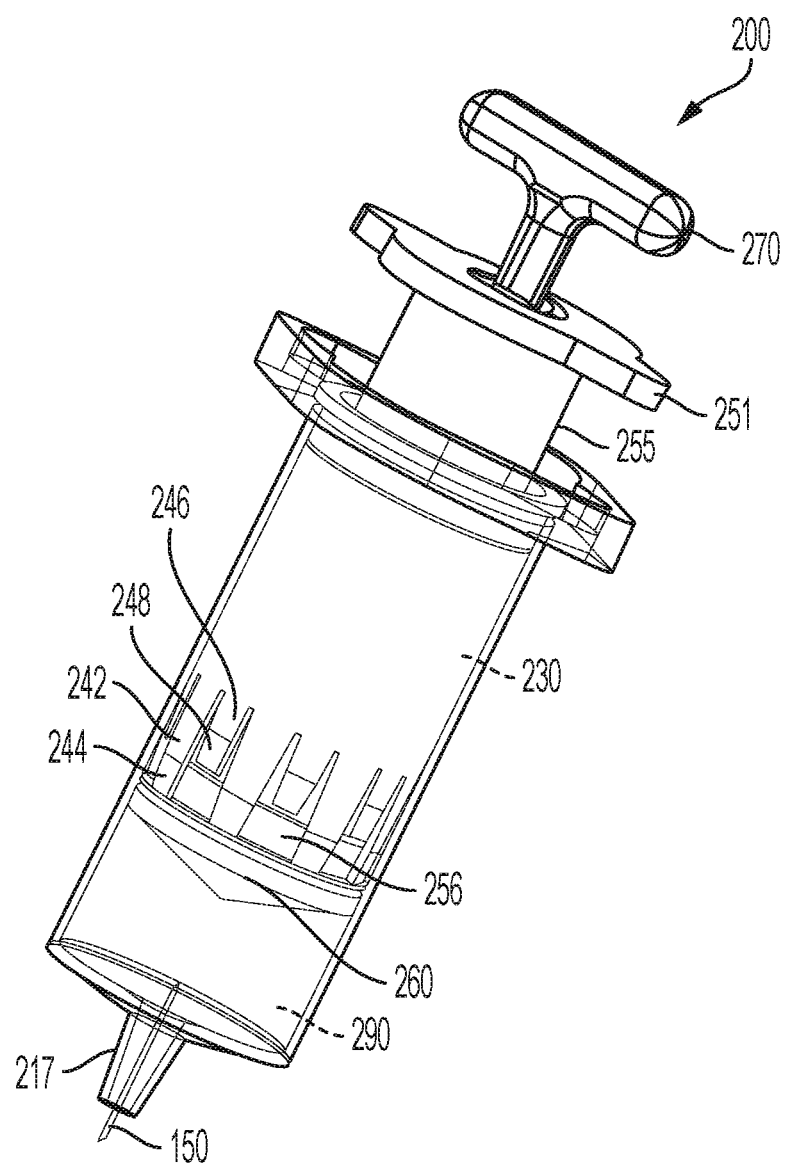
FIG. 20 is a perspective view of the sleeved locking dual-stage syringe of FIG. 16, in a shipment configuration with primary plunger and locking mechanism visible through the external barrel.
Figure 21:
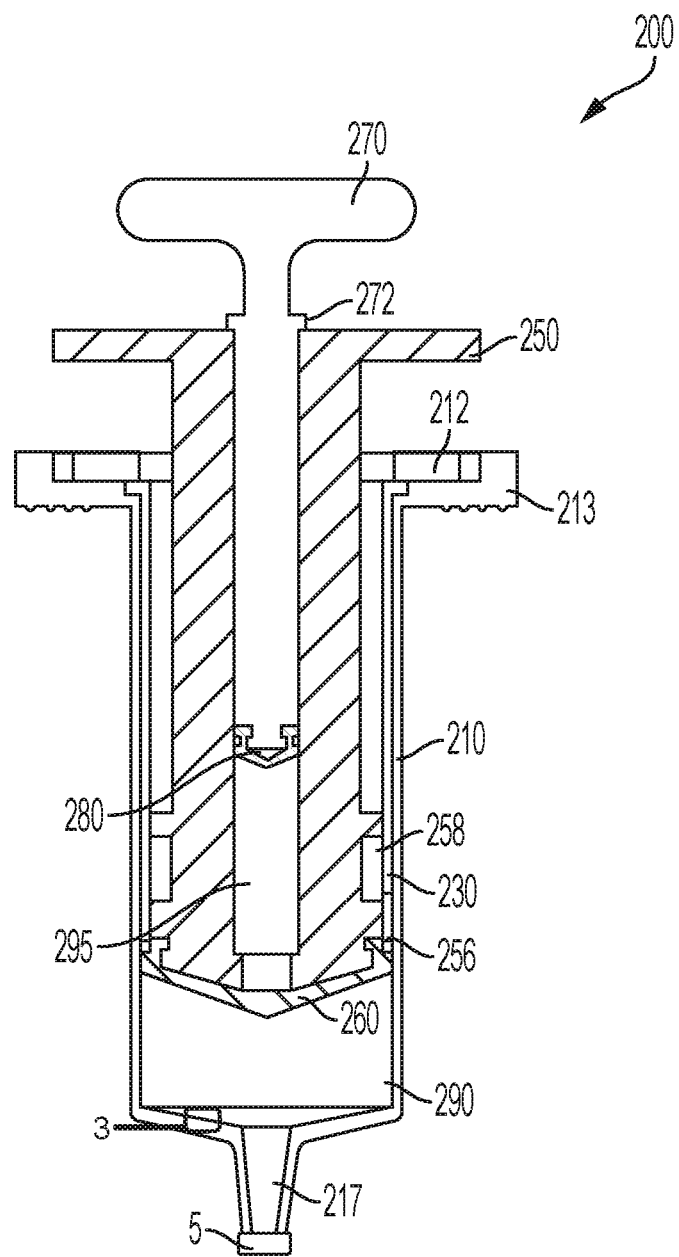
FIG. 21 is a longitudinal cross-section of the sleeved locking dual-stage syringe of FIGS. 19 and 20 in a shipment configuration.

In embodiments, the shipped configuration of FIGS. 19-21 of the sleeved locking dual-stage syringe 200 is a configuration in which the sleeved locking dual-stage syringe 200 may be received by a qualified medical practitioner intending to incorporate the sleeved locking dual-stage syringe 200 into a delivery system for a procedure such as radioembolization. In the shipped configuration, the locking mechanism 230, the primary plunger 250, and the secondary plunger 270 all are inserted to varying extents into the external barrel 210. In particular, the locking mechanism 230 is fully inserted into the external barrel 210 so that the proximal ridge 232 is seated in the external proximal opening 211 of the external barrel 210. The primary plunger 250 is only partially inserted into the external barrel 210, such that some amount of the plunger body portion 255 remains outside the external barrel 210. Furthermore, the primary plunger 250 is inserted only sufficiently far through the locking mechanism, such that the distal stop ring 256 has not passed distally beyond the long-catch ends 244 of the long catches 242 of the locking mechanism 230.

In the shipped configuration of the sleeved locking dual-stage syringe 200, the portion of the primary chamber 290 not filled by the primary plunger 250 initially contains a fluid such as saline, which fluid is intended to flush the system of air at the beginning of the radioembolization procedure. For illustration purposes only, a delivery needle 150 is shown as protruding into the primary chamber 290. In some embodiments, the delivery needle 150 may be attached to the sleeved locking dual-stage syringe 200 in the shipped configuration. In other embodiments the delivery needle 150 may be a component of a delivery system. Some embodiments may include a distal fixture 5. In some embodiments, distal feature 5 may be a gasket, which seals the external distal opening 217 of the external barrel 210 to prevent fluidic communication between the primary chamber 290 and the outside of the external barrel 210, except through the delivery needle 150. In other embodiments, distal feature 5 may be a luer connection, which may be used to connect a the locking dual-stage syringe 200 to a delivery device. In further embodiments, the luer connection may be a male luer connection that has a corresponding female luer connection on a delivery device. In other embodiments, the distal feature 5 may be another connection feature, such as a slip fit, a needless connection port, or any other connection suitable for attachment to a delivery device.

In the shipped configuration of the sleeved locking dual-stage syringe 200, the secondary plunger 270 is inserted into the secondary chamber 295 to such an extent that the insertion stop 272 abuts the proximal wing portion 251 of the primary plunger 250. The portion of the secondary chamber 295 that is not occupied by the secondary plunger 270 is filled with radioembolization beads (not shown). The radioembolization beads are sealed within the secondary chamber by the plunger seal 260. No fluidic communication exists between the primary chamber 290 and the secondary chamber 295.

In embodiments, on receiving a sleeved locking dual-stage syringe 200 in the shipped configuration and optionally attaching the sleeved locking dual-stage syringe 200 to an appropriate delivery system including a reservoir (not shown) that is fluidically connected to the delivery needle 150, the practitioner may pull the secondary plunger 270 proximally to cause both the primary plunger 250 and the secondary plunger 70 to move proximally, thereby expanding the primary chamber 290 and drawing the fluid in the reservoir into the primary chamber 290 by suction force. The practitioner may then push the secondary plunger distally to force the fluid in the primary chamber 290 back toward the reservoir and place the sleeved locking dual-stage syringe 200 into the flushed configuration.

Figure 22:
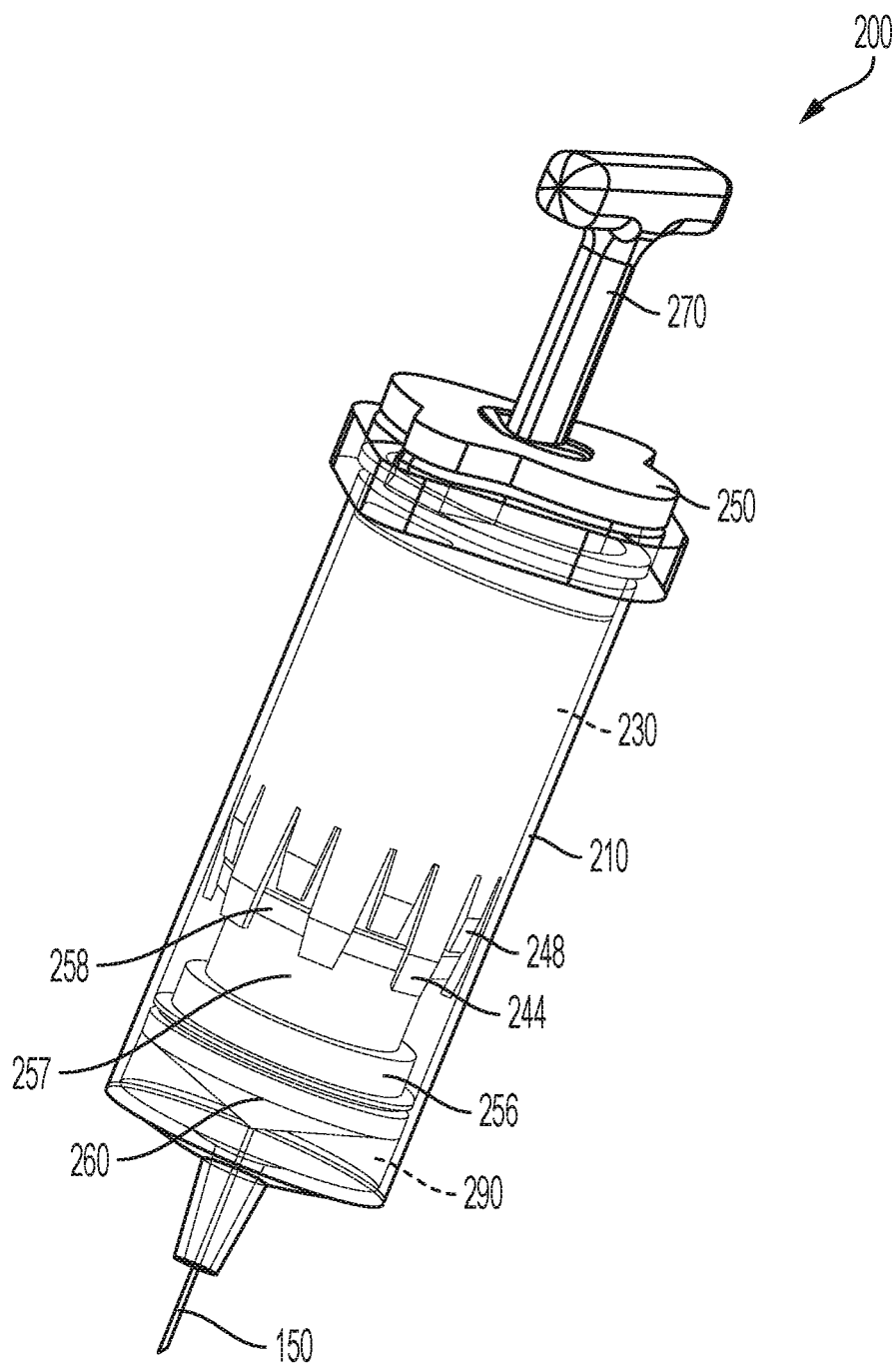
FIG. 22 is a perspective view of a sleeved locking dual-stage syringe according to embodiments, in a flushed configuration with primary plunger and locking mechanism visible through the external barrel.
Figure 23:
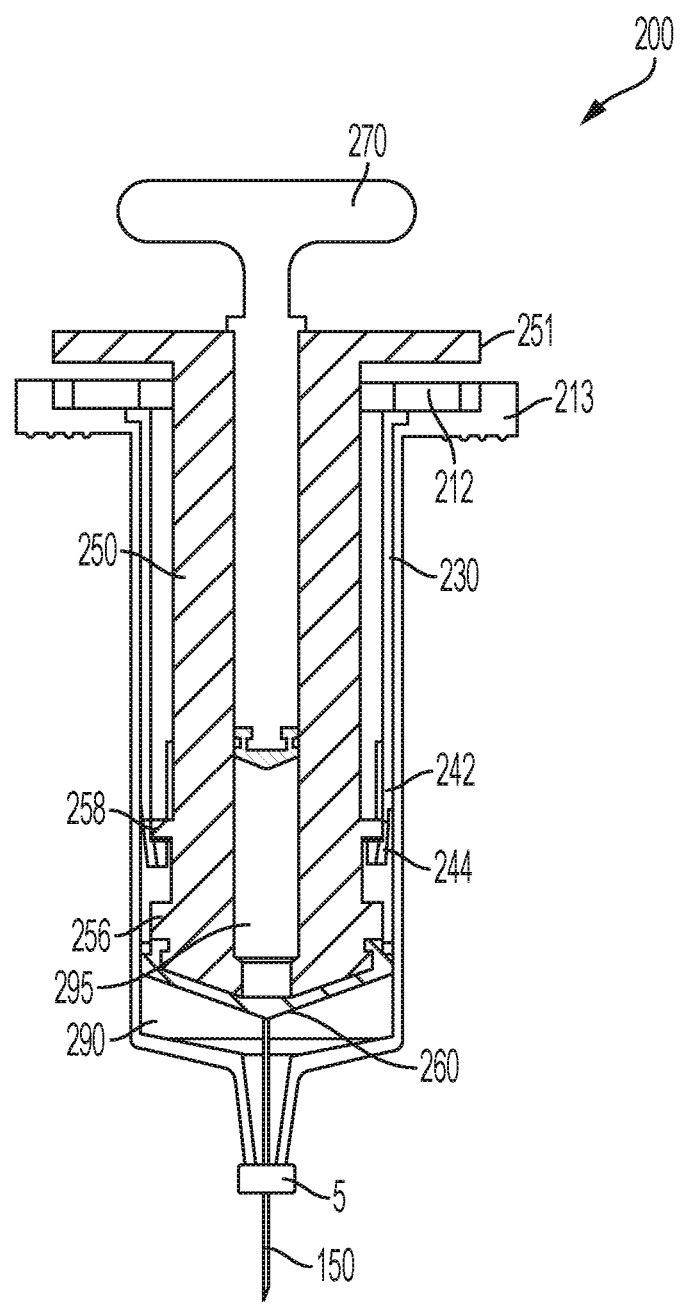
FIG. 23 is a longitudinal cross-section of the sleeved locking dual-stage syringe of FIG. 22 in a flushed configuration.

In embodiments, in the flushed configuration of FIGS. 22-23 of the sleeved locking dual-stage syringe 200, the proximal stop ring 258 has passed the short-catch ends 248 and is substantially even with the long-catch ends 244 but has not passed the long-catch ends 244 in a distal direction. As the proximal stop ring 258 passes the short-catch ends, the short-catch ends 248 may snap inwardly with an audible click to inform the practitioner that the flushed configuration has been reached. Once the audible click has been heard, the primary plunger cannot move proximally beyond the point at which the short-catch ends 48 abut against the proximal stop ring 258. In the flushed configuration of the sleeved locking dual-stage syringe 200, the delivery needle 150 has not pierced through the plunger seal 260 of the primary plunger 250. However, by continued movement of the primary plunger 250 in the distal direction, sleeved locking dual-stage syringe 200 reaches the punctured configuration so that mixing of the radioembolization beads in the secondary chamber 295 of the primary plunger 250 with fluids forced into the reservoir of the delivery system may commence.

Figure 24:
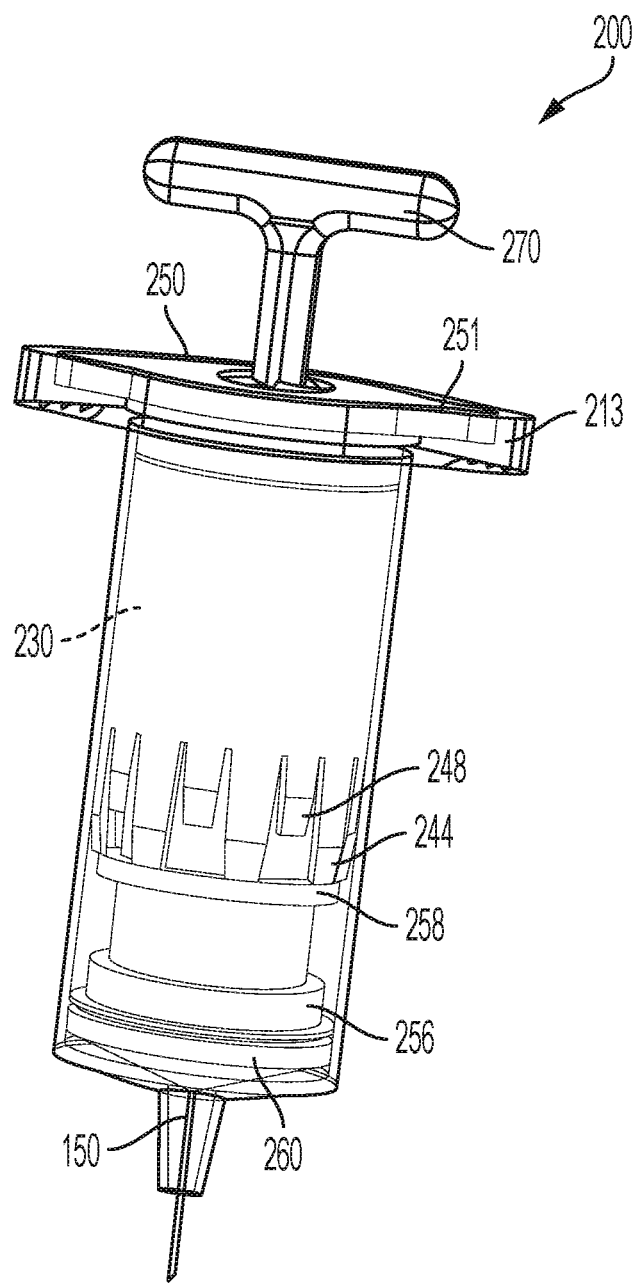
FIG. 24 is a perspective view of a sleeved locking dual-stage syringe according to embodiments, in a punctured configuration with primary plunger and locking mechanism visible through the external barrel.
Figure 25:
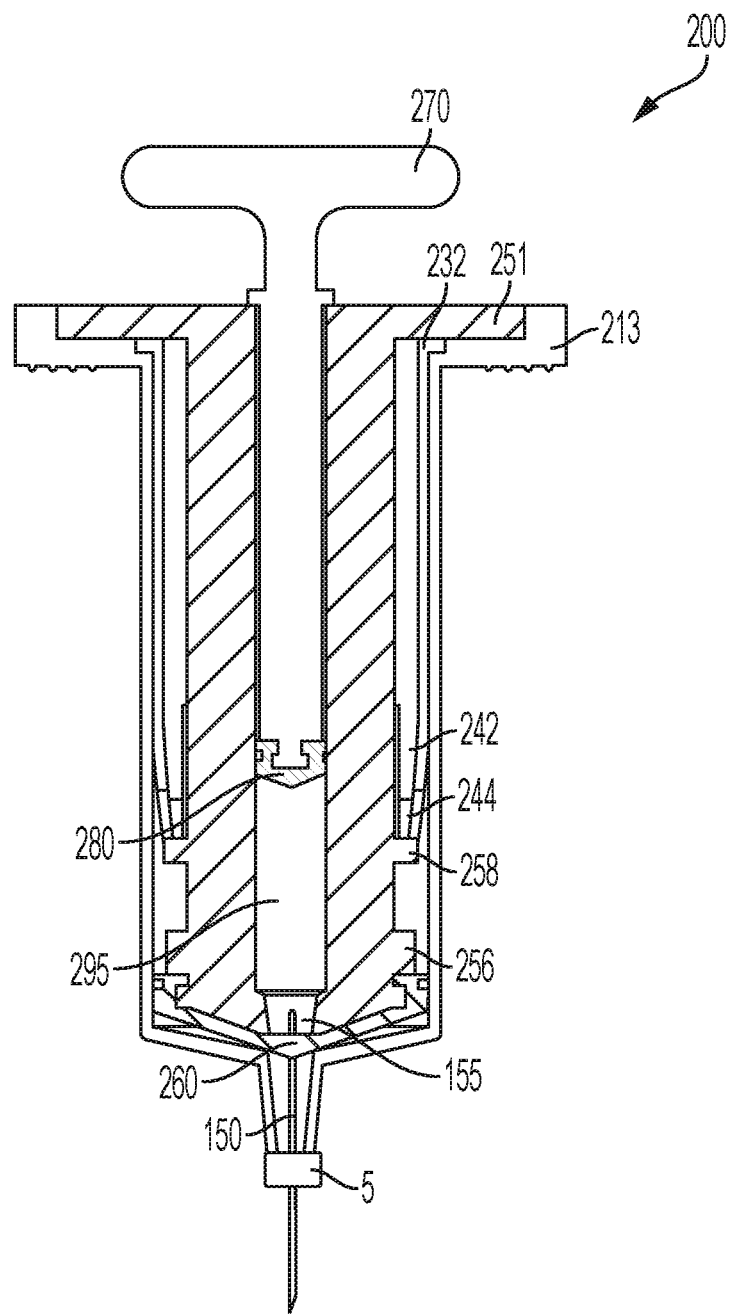
FIG. 25 is a longitudinal cross-section of the sleeved locking dual-stage syringe of FIG. 23 in a punctured configuration.

In embodiments, in the punctured configuration of FIGS. 24-25 of the sleeved locking dual-stage syringe 200, the primary plunger 250 has been inserted to its fullest extent into the external barrel 210, whereby the delivery needle 150 pierces through the plunger seal 260 and a piercing end 155 of the delivery needle 150 is disposed within the secondary chamber 295 containing the radioembolization beads. Furthermore, as the punctured configuration is reached, the proximal stop ring 258 passes the long-catch ends 244 of the locking mechanism 230. In turn, the long-catch ends 244 deflect inwardly by their resilience, resulting in a second audible click to inform the practitioner that the punctured configuration has been reached and the secondary chamber 295 is in fluidic communication with the reservoir of the delivery system outside the sleeved locking dual-stage syringe 100. Accordingly, the primary plunger 250 is locked a second time and proximal movement of the primary plunger 250 is completely prevented.

Once the punctured configuration has been attained during the procedure, the practitioner may unlock the secondary plunger 270, for example, by rotating the secondary plunger 270. The practitioner then may pull the secondary plunger 270 in the proximal direction to expand the secondary chamber 295 and draw fluid from the reservoir of the delivery system into the secondary chamber 295 to be intimately mixed with the radioembolization beads in the secondary chamber 295. When the secondary plunger 270 is pulled proximally to its maximum extent, without removing the secondary plunger 270 from the secondary chamber 295, the sleeved locking dual-stage syringe 200 is in the primed configuration.

Figure 26:
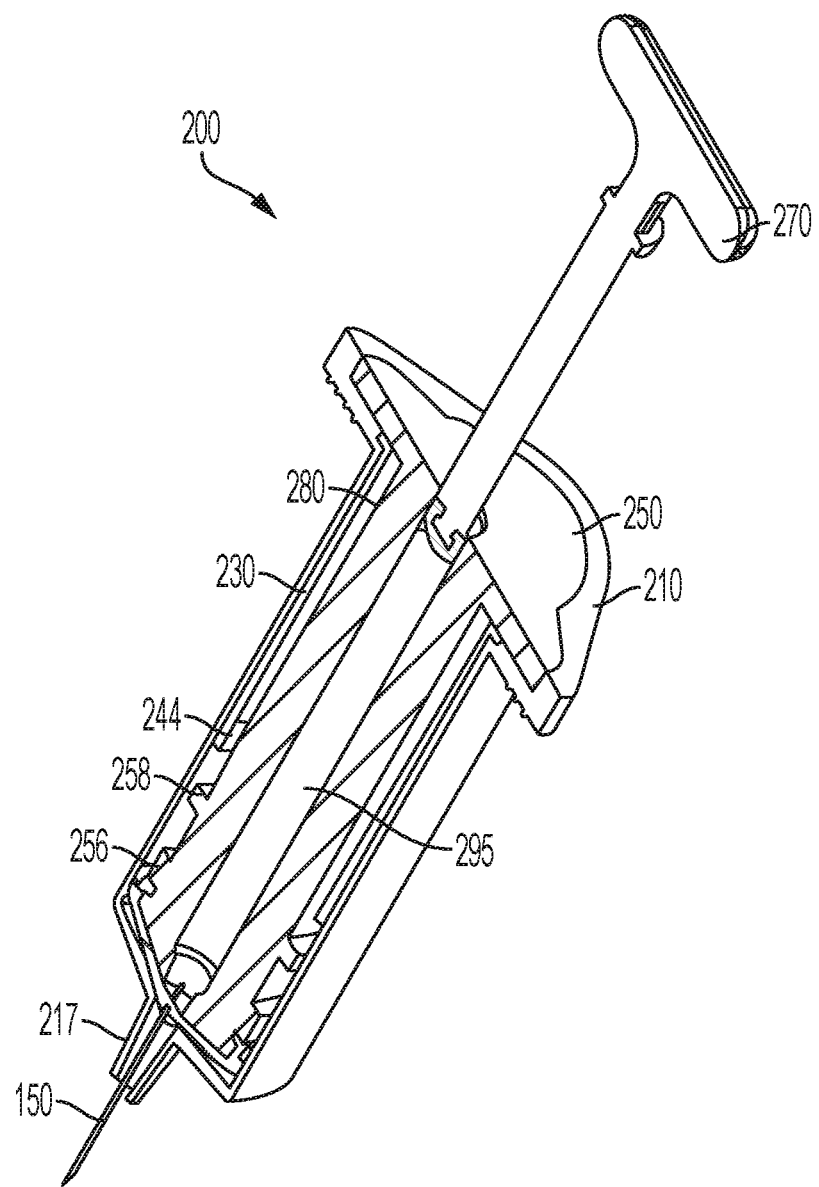
FIG. 26 is a cut-away view of a sleeved locking dual-stage syringe according to embodiments, in a primed configuration with primary plunger and locking mechanism visible through the external barrel.
Figure 27:
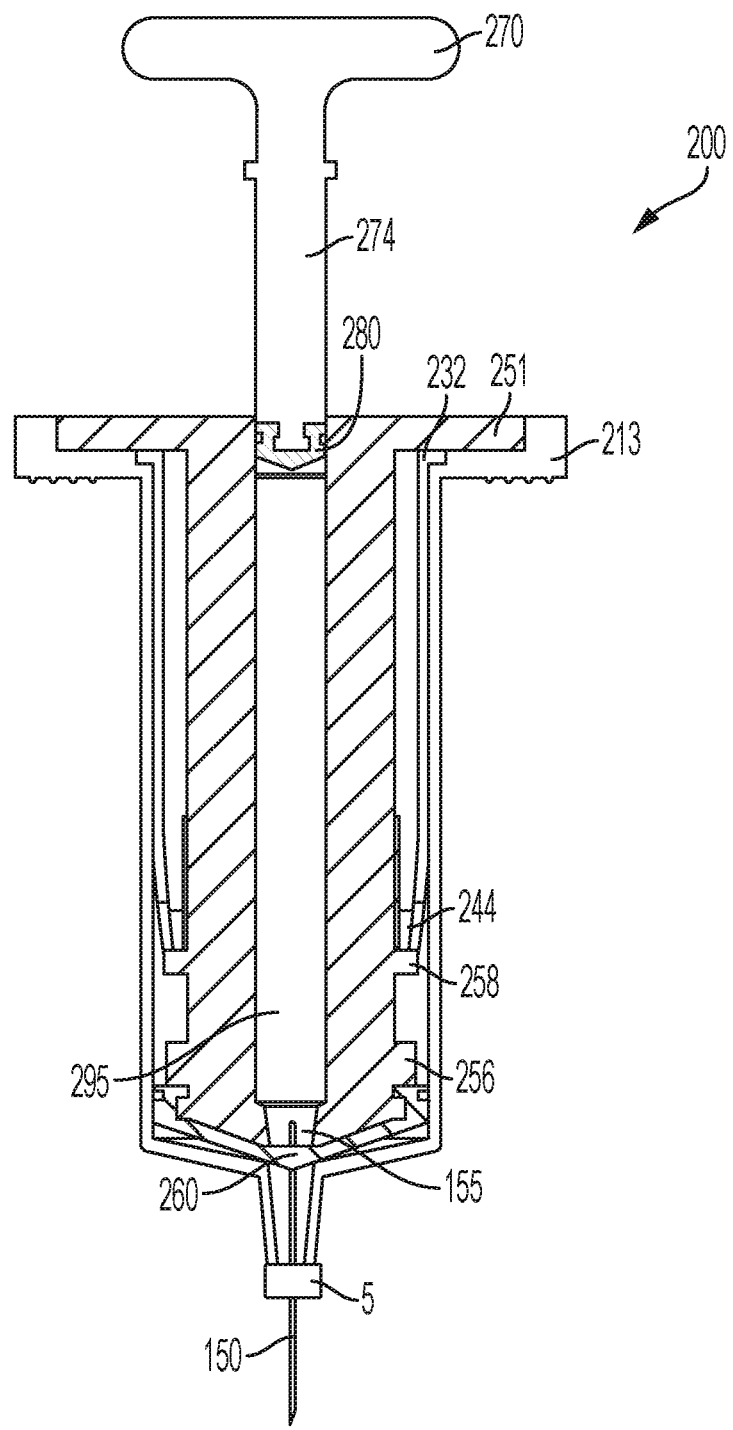
FIG. 27 is a longitudinal cross-section of the sleeved locking dual-stage syringe of FIG. 26 in a primed configuration.

In some embodiments, in the primed configuration of FIGS. 26-27 of the sleeved locking dual-stage syringe 200, the secondary chamber 295 has its maximum volume and contains a treatment mixture such as a mixture of radioembolization beads, for example and an appropriate carrier fluid such as saline, for example. This mixture is the delivery mixture, ready for injection into the patient.

In embodiments, in the delivery configuration of FIGS. 28-29 of the sleeved locking dual-stage syringe 200, the practitioner pushes the secondary plunger 270 in the distal direction to expel the delivery mixture, created when the sleeved locking dual-stage syringe 200 was placed into the primed configuration previously described, distally through the delivery needle 150 and into a delivery system for injection into the patient. The abutting of the insertion stop 272 of the secondary plunger 270 against the proximal wing portion 251 of the primary plunger 250 signals to the practitioner that the secondary plunger 270 has been fully depressed and the dosing of the delivery mixture is complete. Alternatively, the practitioner may pump the secondary plunger 270 multiple times to accomplish multiple cycles of refilling the secondary chamber 295 with fluid and expelling the contents of the secondary chamber 295, so as to ensure that the full dosing of the radioembolization beads has been sent to the delivery system.

Figure 31:
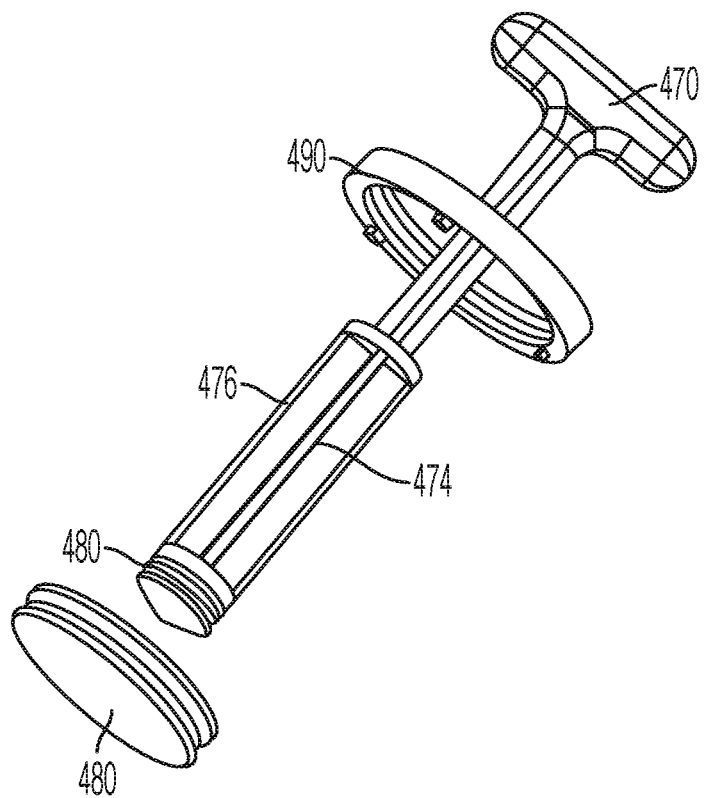
FIG. 31 is a side perspective view of the secondary plunger and sealing member of the turn-key locking dual-stage syringe of FIG. 30.
Figure 32:
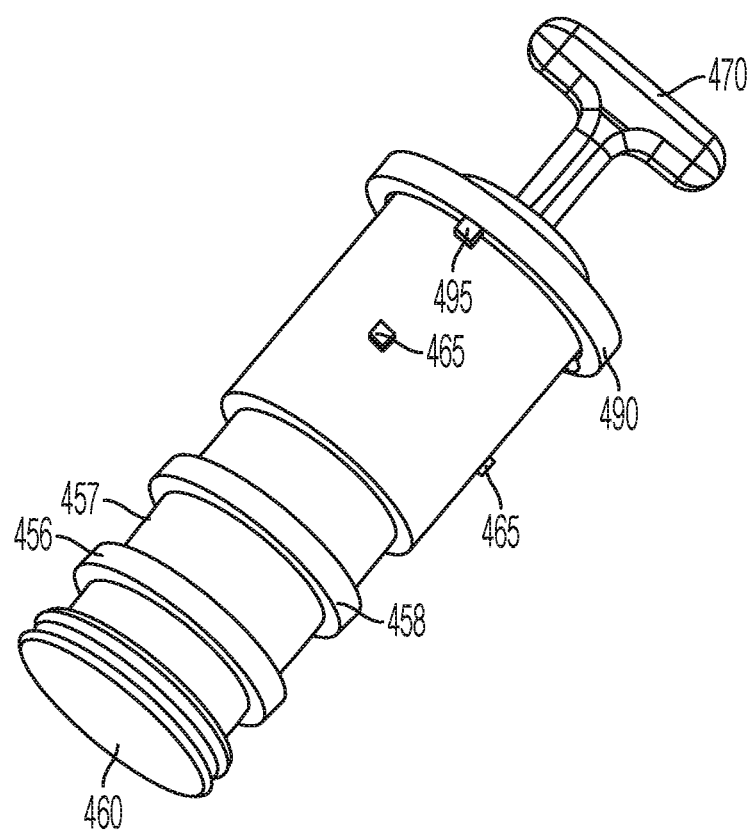
FIG. 32 is a side perspective view of an assembly of the primary plunger, the secondary plunger, and the sealing member of the turn-key locking dual-stage syringe of FIG. 30.

Having described embodiments of the sleeved locking dual-stage syringe 200 in detail, embodiments of a turn-key locking dual-stage syringe 400 will now be described with reference to FIGS. 30-32. Individual components of an embodiment of a turn-key locking dual-stage syringe 400 have previously been described, including the external barrel 410 and the primary plunger 450.

Figure 30:
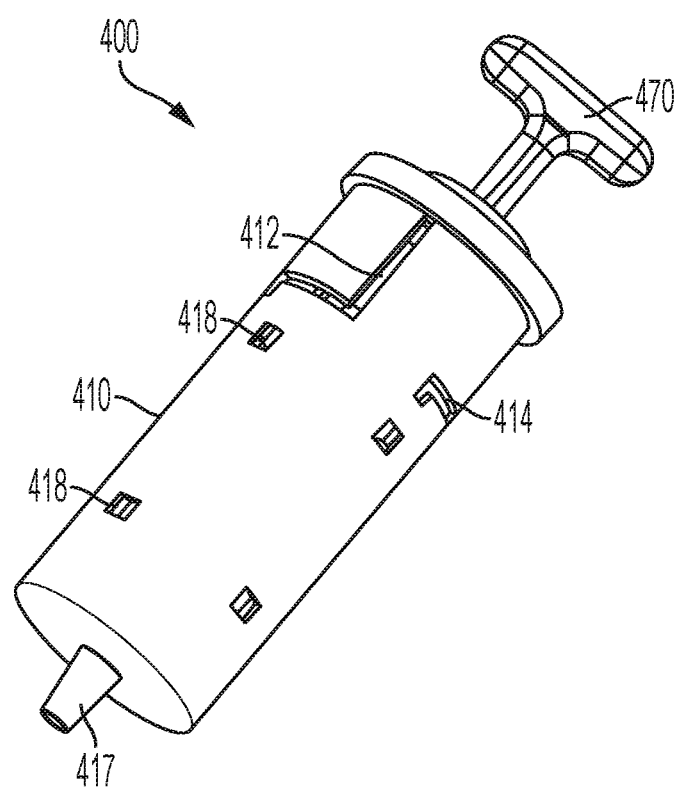
FIG. 30 is a side perspective view of a turn-key locking dual-stage syringe according to embodiments.

As shown in FIG. 30, an exemplary embodiment of the turn-key locking dual-stage syringe 400 fully assembled includes an external barrel 410, a primary plunger 450 (accommodated within the external barrel 410), and a secondary plunger 470.

By way of comparison with embodiments of dual-stage syringes having sleeved locking mechanisms, in place of the locking sleeve 230 of the sleeved locking dual-stage syringe 200 previously described, the turn-key locking dual-stage syringe 400 includes a turn-key locking mechanism. As shown in the embodiment exemplified in FIGS. 30-32 the turn key locking mechanism may include an initial-stage track 412, a intermediate-stage track 414, and a final-stage track 416 within the external barrel 410. In other embodiments, the turn-key locking dual-stage syringe 400 may include one or more additional tracks Like the sleeved locking dual-stage syringe 200 previously described, the turn-key locking dual-stage syringe 400 may include any of the polymers, plastics, metals, or alloys listed above, or it may include other materials such as nylon. Referring now to FIG. 10, embodiments of a primary plunger 450 includes male features 465, which are shaped and sized appropriately to correspond the female features of the turn-key locking mechanism of FIG. 5, previously described. In embodiments male features 465 may be shaped and sized appropriately to travel within the tracks 412, 414, 416 of the external barrel 410.

The intersection of the initial-stage track 412 with the 414 corresponds to an initial stage of the primary plunger. The intersection of the initial-stage track 412 with the intermediate-stage track 414 corresponds to a position of the primary plunger 450 analogous to the flushed configuration of the sleeved locking dual-stage syringe 200, described previously. In the initial stage, the primary plunger is inserted proximal to the initial-stage track 412 and may be freely movable distally or proximally. The intermediate-stage track 414 corresponds to an intermediate stage of the primary plunger. In the intermediate stage, the primary plunger may traverse the intermediate-stage track and is prevented from moving proximally beyond the intermediate-stage track. The physician rotates the secondary plunger 470 to shift the male features 465 across the intermediate-stage track 414 and prepare the turn-key locking dual-stage syringe 400 to enter the delivery configuration. The intersection of the final-stage track 416 with the intermediate-stage track 414 corresponds to a final stage of the primary plunger. A final push of the secondary plunger 470 in a distal direction causes the male features 465 to slide down the final-stage track 416 sufficiently far to cause a delivery needle to pierce the secondary seal 80 of the primary plunger 450. In the final stage, the primary plunger is inserted distal to the intermediate-stage track and is prevented from moving proximally beyond a distal end of the final-stage track. In other embodiments, the turn-key locking dual-stage syringe 400 may include a turn-key locking mechanism that includes one or more additional tracks in the surface of the external barrel 410, which may define one or more additional stages.

Dual-Stage Syringes Having One or More Integrated One-Way Valves

In some embodiments, the dual-stage syringes described herein include integrated one-way valve dual-stage syringe. In some embodiments, the integrated one-way valve dual-stage syringe may be a dual-stage syringe having an integrated one way valve and needle. and needle. In some embodiments, the integrated one-way valve dual-stage syringe may be a dual-stage syringe having two integrated one way valves. Embodiments of the integrated one-way valve dual-stage syringe may be used in any technical setting where it is necessary to delivery two separate and isolated mediums, such as during Transarterial Radioembolization for the treatment of malignant liver tumors.

Referring now to FIGS. 33-36C, embodiments of the integrated one-way valve dual-stage syringe 600 are provided. In some embodiments, the integrated one-way valve dual-stage syringe 600 may include a primary plunger 650, which may be configured to deliver at least two media independently.

Figure 33:
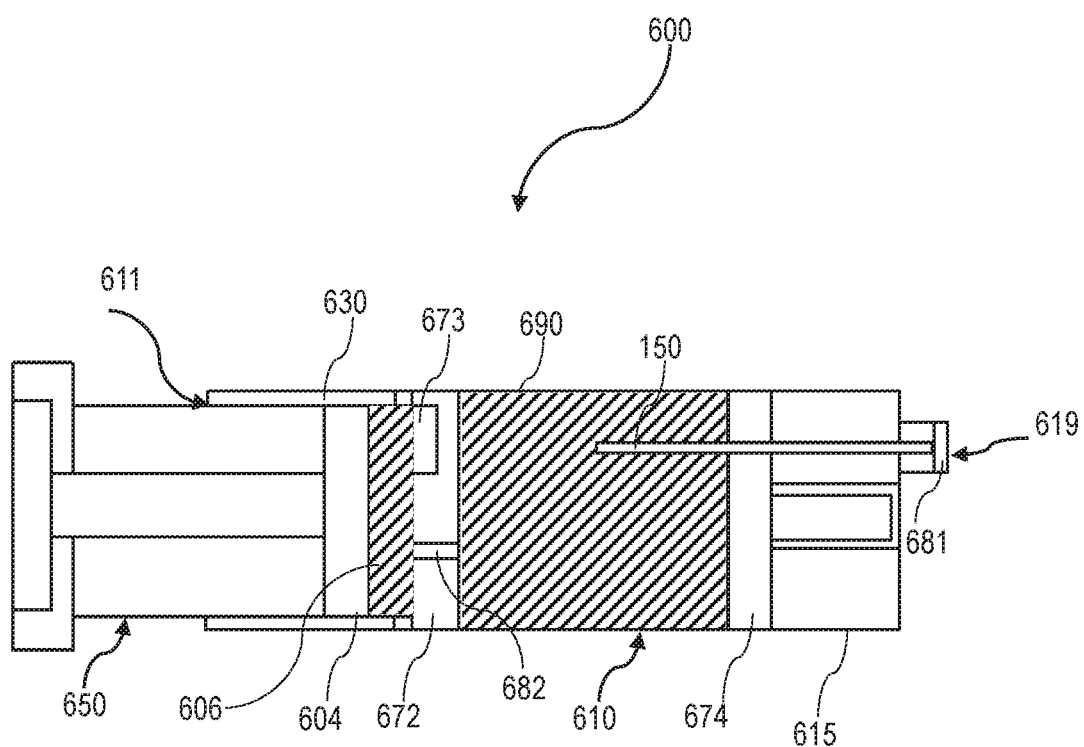
FIG. 33 is a side cross section view of an integrated one-way valve syringe, according to embodiments.
Figure 35:
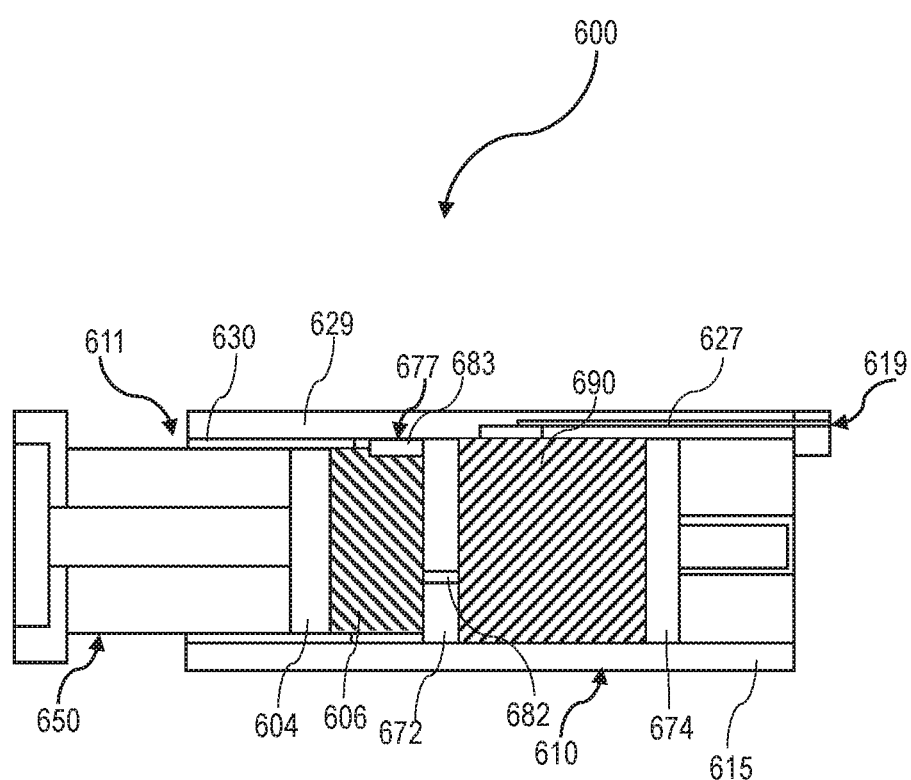
FIG. 35 is a side cross section view of an integrated one-way valve syringe according to embodiments.

Referring to FIGS. 33 and 35, an integrated one-way valve dual-stage syringe 600 is provided according to embodiments. In the embodiment exemplified in FIG. 33, the integrated one-way valve dual-stage syringe 600 may include an external barrel 610, which accommodates a primary plunger 650. The external barrel 610 may have a primary chamber 690 defined through the external barrel 610 from a proximal opening of the external barrel 610 to a distal opening 619 of the external barrel 610. In embodiments, a floating septum plunger 674 may be disposed within the primary chamber 690 of the external barrel 610. In embodiments, a divider 672 may be disposed within the primary chamber 690 of the external barrel 610, which divides the secondary chamber 606 to the primary chamber 690.

In embodiments, the external barrel 610 may be made of various materials such as, for example, polymers, plastics, or metals. Non-limiting example polymers for the external barrel include polycarbonates (PC), polyethylenes (PE), polyethylene terephthalates (PET). Non-limiting example plastics for the external barrel 610 include poly(methyl methacrylate) (PMMA) and composite resins such as polycarbonate loaded with tungsten. Non-limiting example metals and metal alloys for the external barrel 610 include stainless steel, lead, copper, tungsten, aluminum, pewter, and various alloys of any of these. In some embodiments, the external barrel 610 is made of a radiation shielding material such as the plastics or metals previously listed. The radiation shielding material may have a thickness sufficient to ensure that radiation from a radioactive therapeutic material in the integrated one-way valve dual-stage syringe 600 cannot penetrate to the environment or cause safety concerns for personnel operating the integrated one-way valve dual-stage syringe 600. In embodiments, suitable radiation shielding materials may shield operators of the integrated one-way valve dual-stage syringe 600 from beta-particle radiation, from x-rays, or both.

Referring still now to FIGS. 33 and 35, the external barrel 610 may include an external proximal opening 611, an external distal opening 619 opposite the external proximal opening 611, and a body portion 615 between the external proximal opening 611 and the external distal opening 619.

Some embodiments of the integrated one-way valve dual-stage syringe 600 may include one or more locking mechanisms, such as those described previously. For example, the integrated one-way valve dual-stage syringe 600 may include a locking sleeve. An example of an integrated one-way valve dual-stage syringe 600 that includes a locking sleeve 630 is provided in FIGS. 33 and 36. Locking sleeve 630 may be similar to locking sleeve 230. As such, like locking sleeve 230, locking sleeve 630 which may include distal catch members are configured as long catches and short catches alternating around the circumference of the body portion at the distal end of the locking sleeve 630. In further embodiments, the one or more locking mechanisms 630 may allow for greater delivery control and may provide tactile and audio feedback for assurance of when media are changed. In embodiments, the locking mechanisms of the integrated one-way valve dual-stage syringe 600 may be temporary or permanent.

Referring still now to FIGS. 33 and 35, the integrated one-way valve dual-stage syringe 600 may include a primary plunger 650 of the locking-mechanism dual-stage syringe 100. The primary plunger 650 may have a sealed distal end 604 that defines a secondary chamber 606. In embodiments, the primary plunger 650 may be sufficiently narrow to be accommodated by external barrel 610. The primary plunger 650 is may engage the secondary chamber 606 and cause the secondary chamber 606 to function as a plunger to the external barrel 610. This may assure that little or no pressure may be applied to the medium in the secondary chamber 606 during the actuation of the external barrel 610.

In embodiments, the primary plunger 650 may be made of various materials such as, for example, polymers, plastics, or metals. Non-limiting example polymers for the external barrel include polycarbonates (PC), polyethylenes (PE), polyethylene terephthalates (PET). Non-limiting example plastics for the primary plunger 650 include poly(methyl methacrylate) (PMMA) and composite resins such as polycarbonate loaded with tungsten. Non-limiting example metals and metal alloys for the primary plunger 650 include stainless steel, lead, copper, tungsten, aluminum, pewter, and various alloys of any of these. In some embodiments, the primary plunger 650 is made of a radiation shielding material such as the plastics or metals previously listed. The radiation shielding material may have a thickness sufficient to ensure that radiation from a radioactive therapeutic material in the integrated one-way valve dual-stage syringe 600 cannot penetrate to the environment or cause safety concerns for personnel operating integrated one-way valve dual-stage syringe 600. In embodiments, suitable radiation shielding materials may shield operators of the integrated one-way valve dual-stage syringe 600 from beta-particle radiation, from x-rays, or both.

Embodiments of the integrated one-way valve dual-stage syringe 600 may include a one-way valve 682, which is configured to allow flow in only one direction, which may be from the secondary chamber 606 to the primary chamber 690. One-way valve 682 may allow for a medium in a secondary chamber 606 to be mixed with fluid from the primary chamber 690. In further embodiments, the integrated one-way valve dual-stage syringe 600 may allow for a medium in a secondary chamber 606 to be mixed with fluid from the primary chamber 690 multiple times and for the primary chamber 690 to be purged multiple times. In particular, the integrated one-way valve dual-stage syringe 600 may include one or more additional one-way valves, which are each configured to allow flow in only one direction. In particular, the one-way valves may allow for a flow path that mixes the media contained in the primary chamber 690 with the media in the secondary chamber 606 while eliminating the need for secondary or external connections, such as secondary or external connections with one or more additional syringes. In embodiments, the number and sizes of the chambers can vary.

Referring now to FIG. 33, in some embodiments, the integrated one-way valve dual-stage syringe 600 may include and a needle 150 that passes through the floating septum plunger 674 and into the primary chamber 690. This embodiment may include a one way valve 681 at the distal end of the needle 150. In FIG. 33, the divider 672 may include a port 673. In some embodiments, the port 673 may be aligned with the needle 150. In other embodiments, the primary plunger 650, the external barrel 610, or other component may be rotated in order to align the port 673 with the needle 150.

Figure 34C:
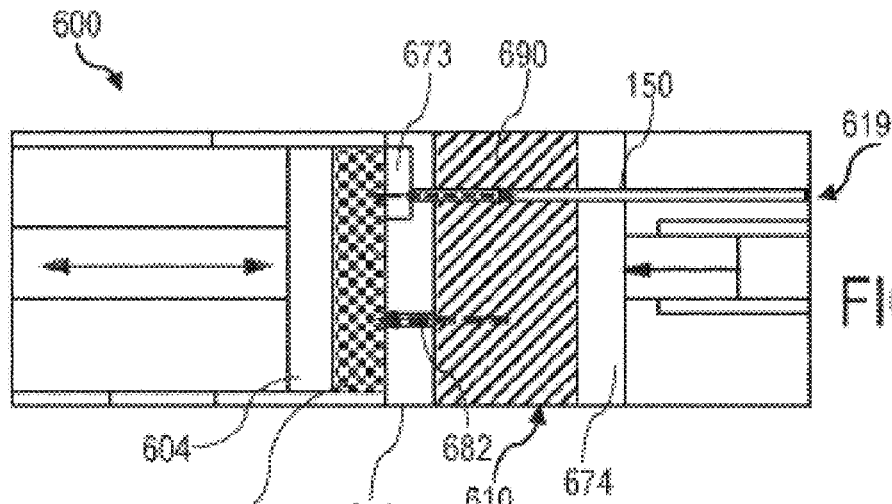
FIG. 34C is a side cross section view of the integrated one-way valve syringe of FIG. 33 in a third stage, according to embodiments.
Figure 34B:
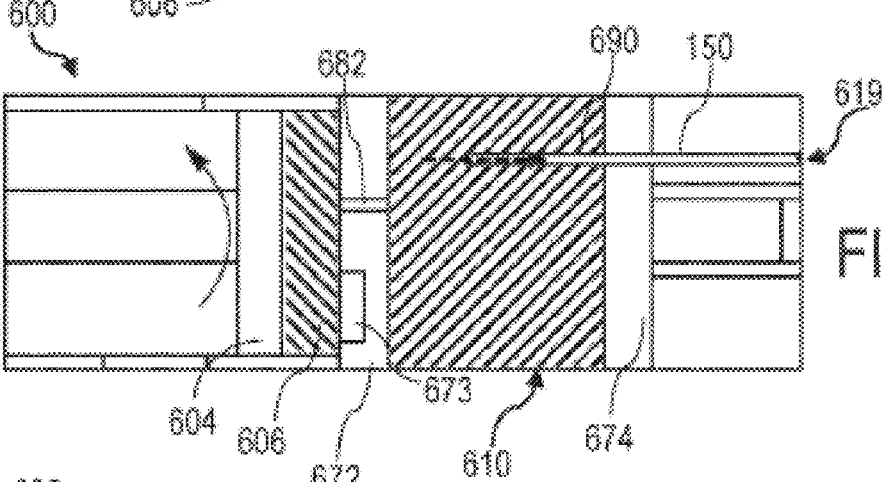
FIG. 34B is a side cross section view of the integrated one-way valve syringe of FIG. 33 in a second stage, according to embodiments.
Figure 34A:
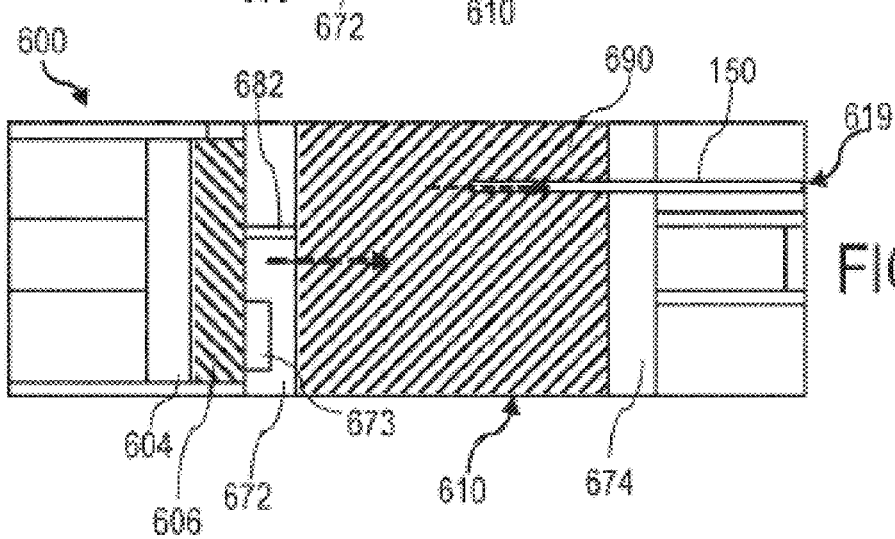
FIG. 34A is a side cross section view of the integrated one-way valve syringe of FIG. 33 in a first stage, according to embodiments.

FIGS. 34A, 34B, and 34C exemplify operation of the embodiment of the integrated one-way valve dual-stage syringe 600 FIG. 33. In FIG. 34A, the primary plunger 650 is advanced distally, which advances the secondary chamber 606 and sealed distal end 604 distally. In FIG. 34B, a first lock of the locking sleeve 630 may be engaged, and the barrel may be rotated to engage a second lock of the locking sleeve 630 and align the needle 150 and the sealed port 673. In FIG. 34C, a second lock of the locking sleeve 630 may be engaged, and the needle 150 may puncture the port 673. In FIG. 34C, media from the primary chamber 690 may flow from the primary chamber 690 through the one-way valve 682, into the secondary chamber 606 to be mixed with fluid from the primary chamber 690. The mixed fluid may then flow through the port 673 through the hollow needle 150, through the one way valve 681, and out the external distal opening 619.

Referring now to FIG. 35, in some embodiments, the integrated one-way valve dual-stage syringe 600 may include a one-way valve 683 on one side of the external barrel 610, which may be allow flow from the secondary chamber 606 to a channel 627 disposed within the sidewall 629 of the external barrel 610.

Figure 36C:
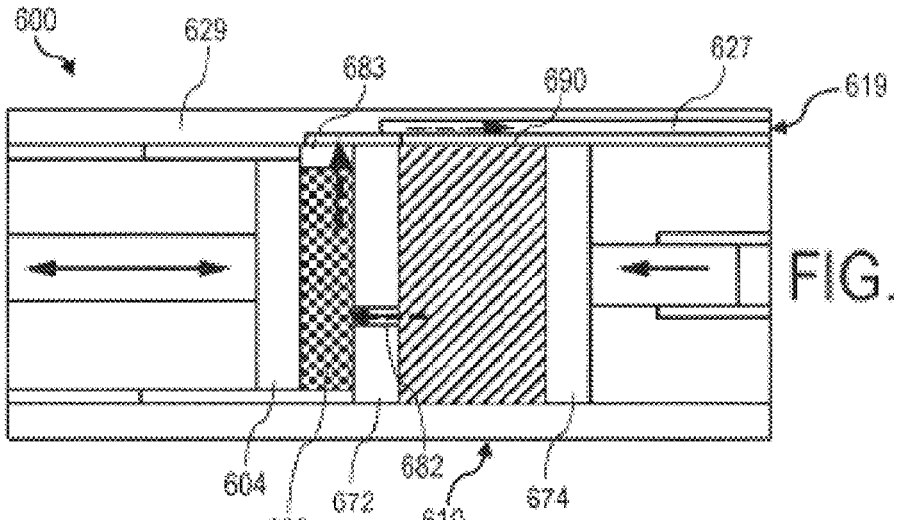
FIG. 36C is a side cross section view of the integrated one-way valve syringe of FIG. 35 in a third stage, according to embodiments.
Figure 36B:
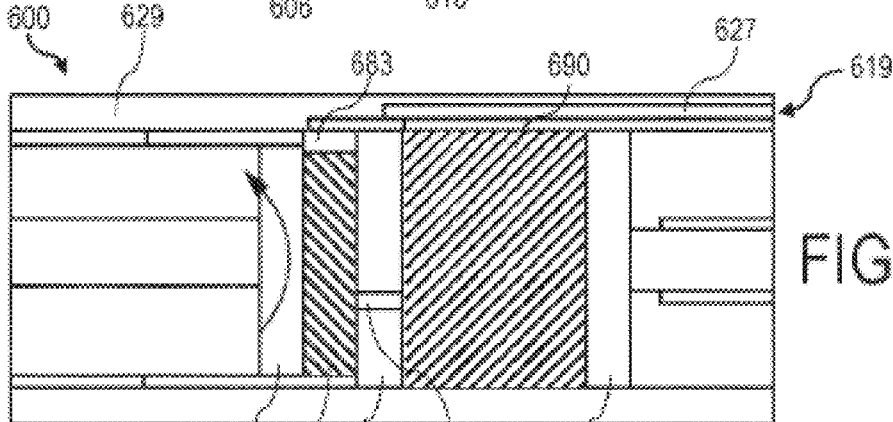
FIG. 36B is a side cross section view of the integrated one-way valve syringe of FIG. 35 in a second stage, according to embodiments.
Figure 36A:
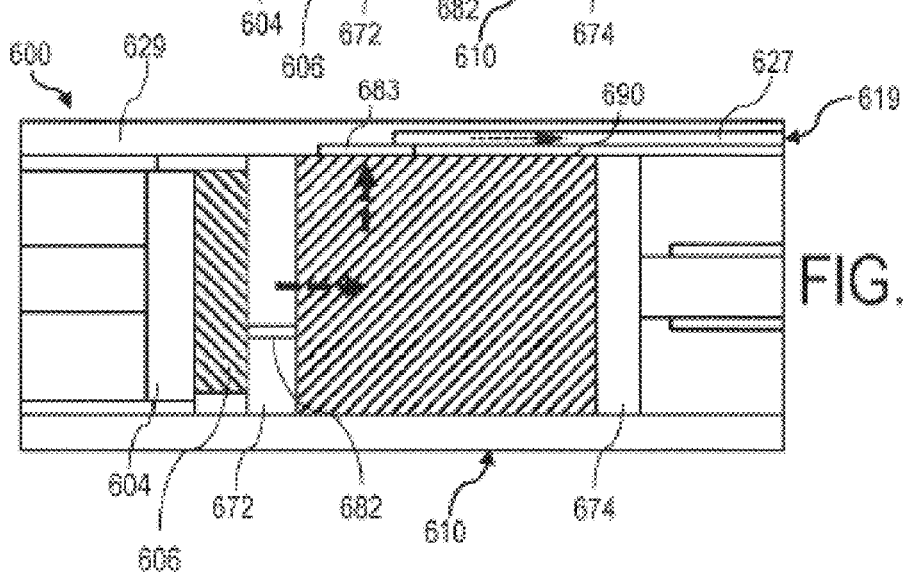
FIG. 36A is a side cross section view of the integrated one-way valve syringe of FIG. 35 in a first stage, according to embodiments.

FIGS. 36A, 36B, and 36C exemplify operation of the embodiment of the integrated one-way valve dual-stage syringe 600 FIG. 35. In FIG. 35A, the primary plunger 650 is advanced distally, which advances the secondary chamber 606 and sealed distal end 604 distally. In FIG. 34B, a first lock of the locking sleeve 630 may be engaged, and the barrel may be rotated to engage a second lock of the locking sleeve 630 and align an opening 677 (see FIG. 35) with the one-way valve 683. In FIG. 34C, a second lock of the locking sleeve 630 may be engaged, and the one-way valve 683 may be aligned so that the secondary chamber 606 is in fluid communication the channel 627 disposed within the sidewall 629 of the external barrel 610. In FIG. 34C, media from the primary chamber 690 may flow from the primary chamber 690 through the one-way valve 682, into the secondary chamber 606 to be mixed with fluid from the primary chamber 690. The mixed fluid may then flow through the one-way valve 683, through the channel 627 through the one way valve 681, and out the external distal opening 619.

In embodiments, the integrated one-way valve dual-stage syringe 600 comprise any biocompatible material such as metals, metal alloys, and polymers. In some embodiments, the integrated one-way valve dual-stage syringe 600 may include polymers such as polycarbonate, polyethylene, and polyethylene terephthalate. In some embodiments, the integrated one-way valve dual-stage syringe 600 may include seals made from any suitable material, such as thermoplastic elastomers, thermoplastic vulcanizates, silicone. In some embodiments, the integrated one-way valve dual-stage syringe 600 may include metals, such as lead, stainless steel, and copper. In other embodiments, the integrated one-way valve dual-stage syringe 600 may be overmolded a material such as thermoplastic elastomers, thermoplastic vulcanizates, or silicone, for example.

In embodiments of the dual-stages syringes described herein, which may include locking-mechanism dual-stage syringes and dual-stage syringes having integrated one-way valves, the one or more safety features may include a distal feature 5 (see FIG. 21), such a gasket, luer connection, slip fit, a needless connection port, or any other connection suitable for attachment to a delivery device. For example, embodiments of the dual-stages syringes described herein, which may include locking-mechanism dual-stage syringes and dual-stage syringes having integrated one-way valves, may include a gasket similar to distal feature 5 of FIG. 21, which seals an external distal opening of the external barrel to prevent fluidic communication between the primary chamber and the outside of the external barrel, except through the delivery needle. Other embodiments of the dual-stages syringes described herein, which may include locking-mechanism dual-stage syringes and dual-stage syringes having integrated one-way valves, may include a luer connection, similar to distal feature 5 (see FIG. 21), which may be used for connection to a delivery device. In further embodiments, the luer connection may be a male luer connection that has a corresponding female luer connection on a delivery device. In other embodiments, the distal feature 5 may be another connection feature, such as a slip fit, a needless connection port, or any other connection suitable for attachment to a delivery device.

In embodiments of the dual-stages syringes described herein, which may include locking-mechanism dual-stage syringes and dual-stage syringes having integrated one-way valves, the dual-stage syringes may include one or more safety features, which may contribute to making embodiments of the dual-stage syringes describe herein suitable for safe and effective delivery of hazardous therapeutic materials. As will be subsequently described in more detail, safety features that may be optionally incorporated into embodiments of the dual-stage syringes described herein may include membrane technology, safety tabs, telemeterized syringe plunger caps, needle features, magnetic walls, and combinations thereof. In some embodiments, referring now to FIG. 4, the distal end 19 may be sealed with a removeable or puncturable material. Similarly, the distal end 419 (see FIG. 5) and the distal end 610 (see FIGS. 33, 35) may be sealed with a removeable or puncturable material.

In embodiments of the dual-stages syringes described herein, which may include locking-mechanism dual-stage syringes and dual-stage syringes having integrated one-way valves, the one or more safety features may include a relief valve or vent, which may serve to relieve pressure from within the syringe, for example, when the primary plunger is distally advanced. In some embodiments, the relief valve or vent 3 may be integrated into the distal end of the external barrel, as shown in FIG. 21.

Figure 37:
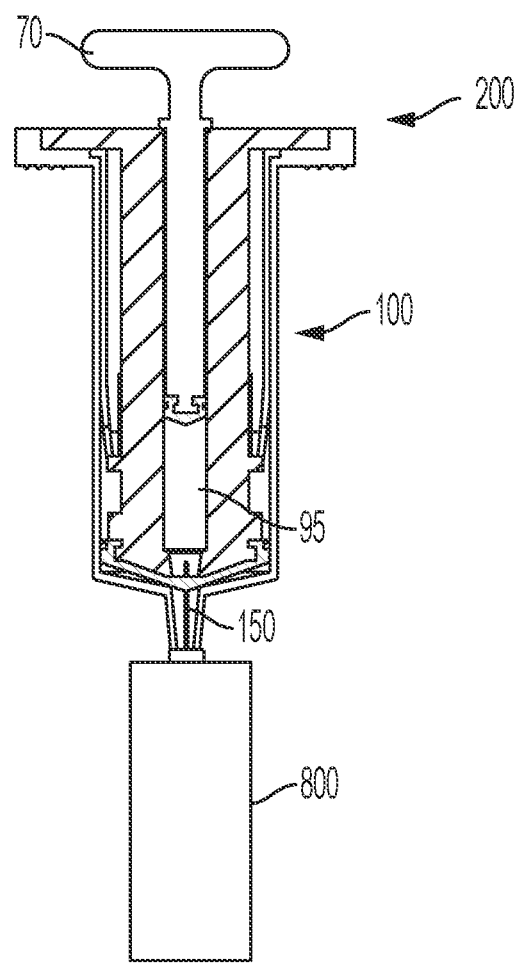
FIG. 37 is a schematic of a sleeved locking dual-stage syringe with membrane technology according to embodiments.

Referring now to FIG. 37, in embodiments of the dual-stage syringes described herein, which may include locking-mechanism dual-stage syringes and dual-stage syringes having integrated one-way valves, the dual-stage syringe may optionally include membrane technology 800 to facilitate purging of air from the system. As shown in FIG. 37, an exemplary embodiment includes a sleeved locking dual-stage syringe 200 in the punctured configuration in fluidic communication with membrane technology 800. In some embodiments, the membrane technology 800 may include components that work together to form dry, leakproof connections, airtight expansion chambers that reduce surface contamination and prevent microbial ingress. In further embodiments, the membrane technology components may be adapted to standards that are compatible with all standard sizes of hazardous drug vials and intravenous connections and tubing.

Figure 38:
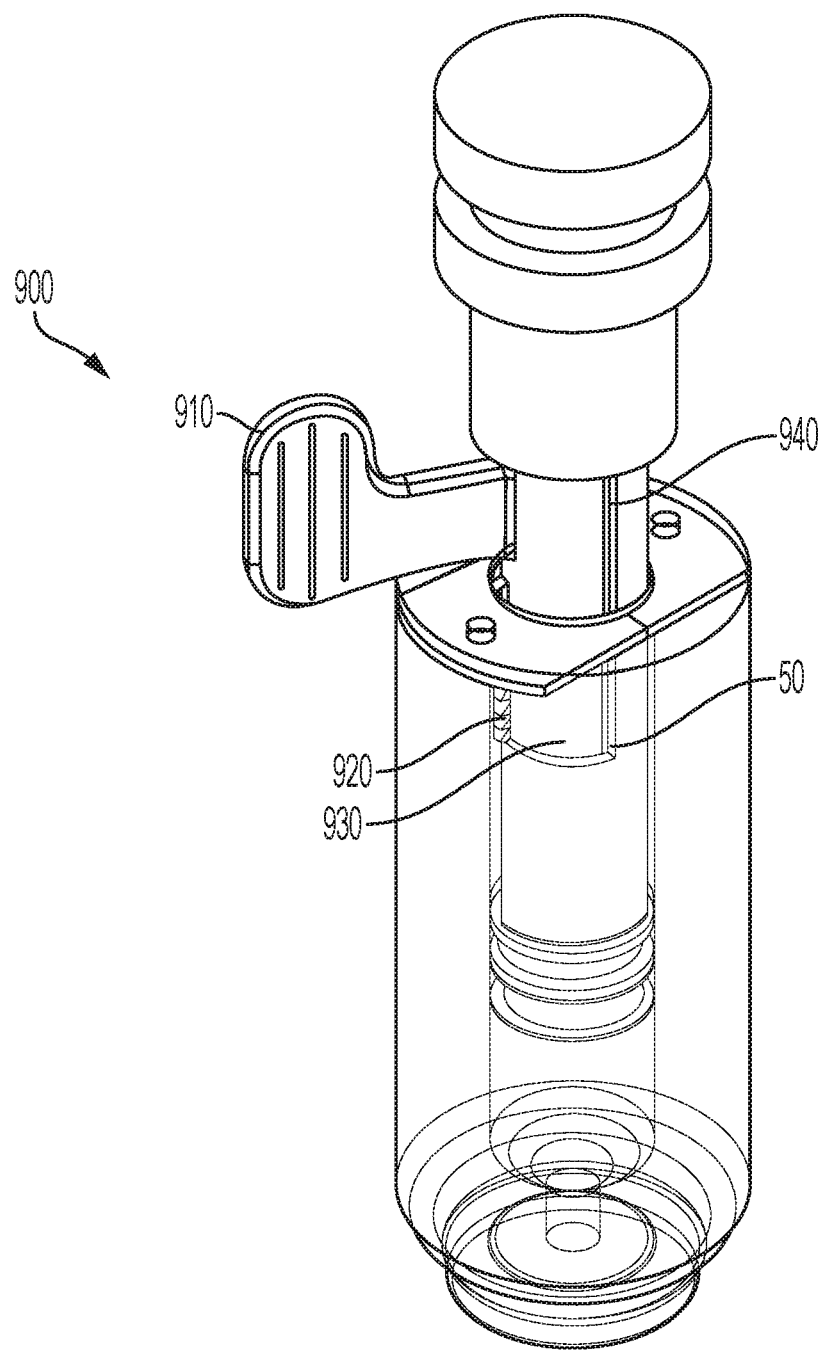
FIG. 38 is a side view of a syringe with a ratcheting safety tab, according to embodiments.
Figure 39:
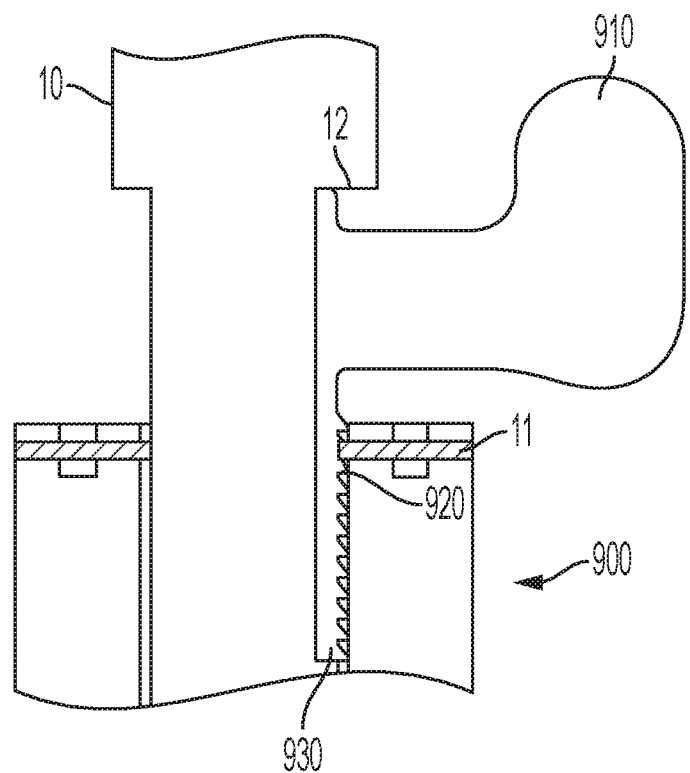
FIG. 39 is a side cross-section view of a syringe with a ratcheting safety tab, according to embodiments.

Referring now to FIGS. 38-39, in embodiments of the dual-stage syringes described herein, which may include locking-mechanism dual-stage syringes and dual-stage syringes having integrated one-way valves, the dual-stage syringe may optionally include a ratcheting safety tab 900 to help mix or suspend pharmaceuticals and particles in a defined volume of solution.

In the context of radioembolization, radioactive particles, such as microspheres, can be transported to a medical facility in a prefilled syringe, such as embodiments of the dual-stages syringes described herein. During this time, the radioactive particles may settle at the bottom of the syringe. Therefore, it is required for the medical professional to draw up a given amount of saline into the syringe to help re-suspend the particles so that the therapeutic fluid comprising the particles has the appropriate concentration for effective delivery. If this suspension is not performed, there may be a risk of the particles either being delivered in a large bolus to the patient and/or there is a risk that the large bolus may clog the administrative tubing set, which may result in misadministration.

Therefore, a ratcheting safety tab 900 may be incorporated into embodiments of the dual-stages syringes described herein to help mix or suspend pharmaceuticals and particles in a defined volume of solution. Referring now to FIG. 38, embodiments of a ratcheting safety tab 900 may include a safety tab 910, connected at one end of safety tab 910 to the primary plunger 50 by a plunger attachment portion 940, which may include one or more angled teeth 920 at the distal end 930 of the ratcheting safety tab 900.

FIG. 39 illustrates a cross-sectional side view of a ratcheting safety tab 900 configured to an embodiments of the dual-stages syringes described herein. In embodiments, the one or more angled teeth 920 may engage one or more retention clips attached to the primary plunger 50. In other embodiments, various mating mechanisms could be used, such as pins and lots, which may engage one or more retention clips attached to the primary plunger 50.

Referring to FIG. 39, as the primary plunger 50 is pulled proximally, one or more angled teeth 920 on the tab 910 slide past the retention clip 11. Additionally, as the angled teeth 920 on the ratcheting safety tab 900 proximally slide past the retention clip 11, and a hard stop results when an attempt is made to advance the primary plunger 50 distally. In embodiments, the primary plunger 50 may be pulled proximally, until each of the one or more angled teeth 920 on the safety tab 910 slide past the retention clip 11. In other embodiments, the geometry may be of any configuration such that primary plunger 50 must be pulled a predetermined distance before the safety tab safety tab 910 may be removed. Once the safety tab 910 is removed, the primary plunger 50 may then be depressed, and the treatment may be administered. In other embodiments, the safety tab 910 may not need to be removed from the primary plunger 50 for the treatment to be administered. Once the primary plunger 50 is pulled beyond the predetermined distance, the user could rotate the safety tab 910 to an "unlocked" or "delivery" position. Once the safety tab 910 is unlocked, the primary plunger 50 may then be depressed, and the treatment may be administered. When the safety tab 910 is locked, the primary plunger 50 cannot be depressed, and the treatment cannot be administered.

In embodiments, the ratcheting safety tab 900 may include any biocompatible material such as metals, metal alloys, and polymers. In some embodiments, the ratcheting safety tab 900 may include polymers such as polycarbonate, polyethylene, polypropylene and polyethylene terephthalate. In some embodiments, the ratcheting safety tab 900 may include seals made from any suitable material such as thermoplastic elastomers, thermoplastic vulcanizates, or silicone, for example. In some embodiments, the ratcheting safety tab 900 may include metals, such as lead, aluminum, stainless steel, and copper.

Figure 40A:
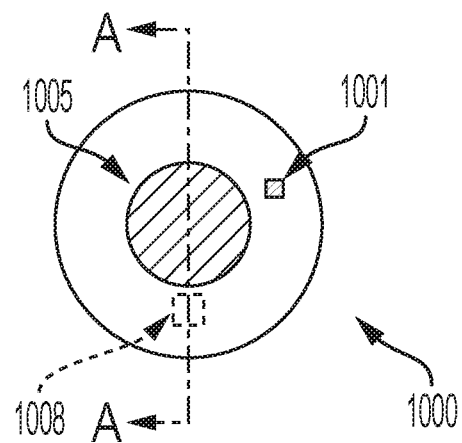
FIG. 40A is top view of a telemeterized syringe plunger cap, according to embodiments.
Figure 40B:
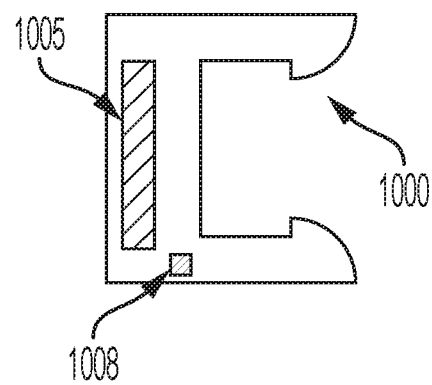
FIG. 40B is section view of a telemeterized syringe plunger cap, according to embodiments.
Figure 40C:
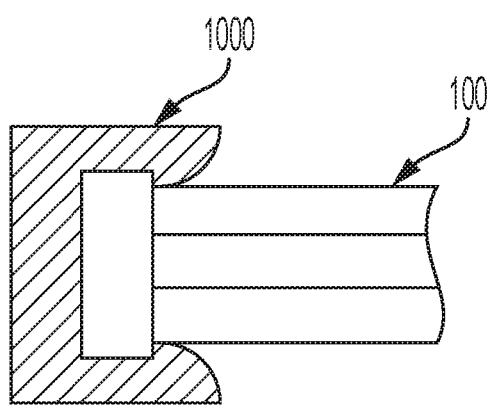
FIG. 40C is a section view of a telemeterized syringe plunger cap assembled on a syringe plunger, according to embodiments.

Referring now to FIGS. 40A, 40B, and 40C, in some embodiments, the dual-stage syringes described herein may include a telemeterized syringe plunger cap 1000.

During transarterial radioembolization procedures, changes in injection pressure and flow rate can impact the safety, efficacy, and patient comfort of medical devices and systems. As stated previously, for example, liver cancer can be treated with embolizing beads in conjunction with chemotherapy. In this scenario, the vasculature has been structurally weakened from chemotherapy. Thus, the injection pressure the physician can safely use may be limited. However, the efficacy and dispersion of embolizing beads is correlated with increased injection pressure and flow rates.

Therefore, in some embodiments, the dual-stage syringes described herein may include a telemeterized syringe plunger cap 1000, which may monitor and record the injection pressure and flow rate of the embolizing beads delivered from the dual-stage syringe and allow for the desired dispersion to be achieved without damaging the vasculature. In embodiments, a telemeterized syringe plunger cap may provide real-time feedback to the medical professional, and the resulting data could be correlated to patience outcomes, serve for quantitate training, and provide inputs to automated systems and ergonomic devices. In some embodiments, one or more of a pressure sensor and/or a displacement sensor of a telemeterized syringe plunger cap may sense a corresponding movement of the syringe plunger as a sensed plunger movement; when the syringe plunger is translationally moved in a translational direction, such that movement in the translational direction one of proximally or distally advances the syringe plunger. In embodiments, this then generates via the one or more of a pressure sensor and a displacement sensor of the telemeterized syringe plunger cap, one or more output signals based on the sensed plunger movement. This then generates, via a processor, at least one of a flow rate of the administered fluid, a flow amount of the administered fluid, a pressure of the administered fluid, a pressure applied to the syringe plunger, or the translational direction of movement of the syringe plunger with respect to the syringe based on the one or more output signals. In some embodiments, at least one of the flow rate of the administered fluid, the flow amount of the administered fluid, the pressure of the administered fluid, or the translational direction of movement of the syringe plunger with respect to the syringe may be displayed on a display communicatively coupled to the syringe.

FIG. 40A shows a top view of a telemeterized syringe plunger cap 1000. In embodiments, the telemetered syringe plunger cap 1000 may include a wireless transmitter 1008, a pressure sensor 1005 and displacement sensor 1001 housed in a cap that attaches to the proximal end of a plunger or a syringe 100. FIG. 40B shows a section view along A-A shown in FIG. 40A. FIG. 40C shows the telemeterized syringe plunger cap 1000 attached to the proximal end of a plunger or a syringe 100. In other embodiments, the mechanism for engagement between the telemeterized syringe plunger cap 1000 and the syringe 100 may be, for example, mechanical, chemical, or magnetic. In some embodiments, the wireless transmitter 1008 may be a Bluetooth transmitter. In some embodiments, the displacement sensor 1001 may include an accelerometer. In some embodiments, the cap may be made from polyethylene.

In an exemplary embodiment, the telemeterized syringe plunger cap 1000 may be attached to the proximal end of a plunger or a syringe 100 that contains radioactive materials, such as microspheres. As the physician applies pressure to the top of the syringe, the telemeterized syringe plunger cap 1000 will deflect, and the pressure will be measured by the internal pressure sensor 1005. As the syringe 100 translates forward, the displacement sensor 1001 will register the motion. The information from both the pressure sensor 1005 and the displacement sensor 1001 may be wirelessly transmitted in real time to a computer or smart device where the information may be viewed and stored. Once the procedure has been completed, the telemeterized syringe plunger cap 1000 may be discarded or recovered for sterilization and reuse. In some embodiments, the telemeterized syringe plunger cap 1000 may communicate with other devices by various communication means including Bluetooth, WiFi, and wired connections.

In other embodiments, the telemeterized syringe plunger cap 1000 may include any number of sensors of varying types, such as capacitance sensors, resistance sensors, laser sensors, and optical sensors, which may produce the same outputs previously described. In other embodiments, the telemeterized syringe plunger cap 1000 may include any number of sensors of varying types, such as RFID tags and temperature sensors, which may produce additional outputs or labeling. In some embodiments, additional sensors may be added to monitor withdraw forces, pressures, or rates.

The telemeterized syringe plunger cap 1000 may include different display modalities, such as LED, projection, and tactile display modalities. In other embodiments, the telemeterized syringe plunger cap 1000 may include alarm features, such as flashing lights, sounds, vibrations.

In embodiments, the telemeterized syringe plunger cap 1000 may include any biocompatible material such as metals, metal alloys, and polymers. In some embodiments, the telemeterized syringe plunger cap 1000 may include polymers such as polycarbonate, polyethylene, polypropylene and polyethylene terephthalate. In some embodiments, the telemeterized syringe plunger cap 1000 may include seals made from any suitable material such as thermoplastic elastomers, thermoplastic vulcanizates, silicone. In some embodiments the telemeterized syringe plunger cap 1000 may include polyoxymethylene and acrylonitrile butadiene styrene. In some embodiments, the telemeterized syringe plunger cap 1000 may include metals, such as lead, aluminum, stainless steel, and copper.

In some embodiments, the external barrel 10 of embodiments of the dual-stage syringes described herein may include one or more needles that may be attached to or mounted on the external barrel near the external distal opening 19 of the external barrel 10.

In some embodiments, a magnetic component may be incorporated into one or more individual components of the dual-stage syringes so that the magnetic components such individual components may produce one or more magnetic fields. For example, in some embodiments, the primary plunger may include one or more magnetic components. Referring back to FIG. 7, the primary plunger 50 may have a secondary chamber defined through the primary plunger 50 from a proximal opening of the primary plunger 50 to a sealed distal end of the primary plunger 50. The primary plunger 50 may include one or more magnetic components in the plunger body portion 55 so that the magnetic components included in the plunger body portion 55 may produce a magnetic field. As subsequently described in more detail, the one or more magnetic components may produce a magnetic field that repels a diamagnetic material of a plurality of microspheres. This repulsion between the one or more magnetic components and the diamagnetic material of the plurality of microspheres may cause the plurality of microspheres to levitate within embodiments of the dual-stage syringe. As a result, the magnetic components incorporated into embodiments of the dual-stage syringes described herein may reduce interaction or binding of radiotherapeutic microspheres with the dual-stage syringes, which may prevent browning and/or embrittlement of the materials used to form embodiments of the dual-stage syringes described herein. Additionally, in some embodiments, the magnetic components incorporated into components of the dual-stage syringes described herein may produce non-uniform magnetic fields, for example, along the plunger body portion 55 of the primary plunger 50, which may facilitate the mixing of radiotherapeutic microspheres in a suspension medium such as saline.

In embodiments, the dual-stage syringes may include any suitable gamma compatible material. A gamma compatible material may be any radiation-stable, medical-grade polymer material. The radiation stability of the gamma compatible material may be dependent on the tolerance level of the particular type of medical grade polymer material. Once the container material absorbs a radiation dose that exceeds the container material's tolerance level, browning or embrittlement of the dual-stage syringe may occur. Exemplary gamma compatible materials include, but are not limited to, thermoplastics, including acrylonitrile/butadiene/styrene, aromatic polyesters, cellulosics, fluoropolymers, polyacetals, polyacrylics, polyamides, polyethylenes polyimides, polymethylpentene, polyphenylene sulfide, polypropylenes, polystyrenes, polysulfones, polyurethanes, polyvinylbutyral, polyvinylchloride, polyvinylidene chloride, styrene/acrylonitrile; thermosets including allyl digylcol carbonate, epoxies, phenolics, polyesters, polyurethanes, and elastomers including butyl, ethylene-propylene diene monomer, fluoro elastomers, natural rubbers, nitriles, polyacrylics, polychloroprenes, silicones, styrene-butadienes, and urethanes. The radiation tolerance of the elastomers may be affected by the base polymer and the curing system used. In some embodiments, the dual-stage syringe may be made from a gamma compatible material with a tolerance level of from about 5 kGy to about 100,000 kGy, from about 5 kGy to about 10,000 kGy, from about 5 kGy to about 5,000 kGy, from about 5 kGy to about 1,000 kGy, from about 5 kGy to about 500 kGy, from about 5 kGy to about 100 kGy, from about 100 kGy to about 100,000 kGy, from about 100 kGy to about 10,000 kGy, from about 100 kGy to about 5,000 kGy, from about 100 kGy to about 1,000 kGy, from about 100 kGy to about 500 kGy, from about 500 kGy to about 100,000 kGy, from about 500 kGy to about 10,000 kGy, from about 500 kGy to about 5,000 kGy, from about 500 kGy to about 1,000 kGy, from about 1,000 kGy to about 100,000 kGy, from about 1,000 kGy to about 10,000 kGy, from about 1,000 kGy to about 5,000 kGy, from about 5,000 kGy to about 100,000 kGy, from about 5,000 kGy to about 10,000 kGy, or from about 10,000 kGy to about 100,000 kGy.

In embodiments, the dual-stage syringe may include one or more magnetic fields. The one or more magnetic fields of the dual-stage syringe may interact with the plurality of microspheres in a manner that prevents direct contact of the plurality of microspheres to the dual-stage syringe. In some embodiments, the one or more magnetic fields of the dual-stage syringe may interact with the plurality of microspheres in a manner that facilitates mixing of the plurality of microbeads. The mixing may, at least in part, be facilitated by the shape of the dual-stage syringe. In embodiments, the strength, location, and pattern of the one or more magnetic fields of the dual-stage syringe may vary. The magnetic fields may be of sufficient magnitude to levitate or repel the plurality of microspheres off the surface of the dual-stage syringe. This magnitude may be depend on various factors, including the radiation tolerance of the materials included in the dual-stage syringe; the amount of therapeutic agent in the microsphere, more specifically, the amount of radiotherapeutic material in the microsphere; the type of therapeutic agent in the microsphere, more specifically, the amount of radiotherapeutic material in the microsphere; the amount (mass) of microsphere material, the type of microsphere material, the amount (mass) of diamagnetic material in the microsphere, the type of diamagnetic material in the microsphere, and combinations of these factors. The magnetic fields may be of sufficient magnitude to levitate or repel the plurality of microspheres at a height sufficient to prevent browning or embrittlement of the dual-stage syringe. Without being bound by theory, because the dose is reduced by $1/R^2$, relatively small changes in distance can have a substantial impact on the dose absorbed by the dual-stage syringe.

In some embodiments, multiple magnetic fields may be present within the dual-stage syringe as a result of magnetic components incorporated within features of the dual-stage syringe. The multiple magnetic fields may have varying strengths. For example, at least a portion of the magnetic fields of the dual-stage syringe may be of a lesser strength, and at least a portion of the magnetic fields of the dual-stage syringe may be of a greater strength. The varying strengths of the magnetic fields of the dual-stage syringe may facilitate mixing of the plurality of microspheres within the dual-stage syringe.

In embodiments, the magnetic fields of the dual-stage syringe may be produced by incorporating one or more magnetic components into the walls of the dual-stage syringe's individual components. In other embodiments, the magnetic fields of the dual-stage syringe may be produced by surrounding the dual-stage syringe with one or more magnetic components. When the walls of the containers described herein comprise one or more magnetic components, the walls may comprise any number of individual magnetic components (e.g., one, two, three, four, five, six, seven, or eight or more, etc.). Each magnetic component may be fixed in or on the dual-stage syringe by any suitable method. For example, in some variations one or more magnetic components may be embedded in, adhered to, or friction-fit within the dual-stage syringe by any suitable manufacturing methods, including by painting, over-molding, printing, or gluing the one or more magnetic components onto the dual-stage syringe. In embodiments where one or more magnetic components surround the dual-stage syringe, each magnetic component may not be fixed in or on the dual-stage syringe, so the magnetic fields produced by the magnetic components may be mobile. In further embodiments where one or more magnetic components surround the dual-stage syringe, each magnetic component may be embedded in, adhered to, or friction-fit within a casing, cover, or other external component that surrounds at least a portion of the dual-stage syringe.

In embodiments, the magnetic component may include a permanent magnet. The magnet may be made of any suitable material capable of generating a magnetic field. In some embodiments, the magnetic components may be permanent magnets made out of ferromagnetic materials. For example, in some variations, the magnetic components may comprise one or more rare-earth magnets, cobalt, gadolinium, iron, nickel, alloys of these metals with or without other metals such as alnico, chemical compounds such as ferrites, or a combination of any of these metals or their alloys. In further embodiments, the rare-earth magnets may include samarium cobalt magnets or neodymium magnets.

In embodiments, the magnetic component may include an electromagnet. When a magnetic component comprises an electromagnet, the electromagnet may be selectively activated to produce a magnetic field. For example, when embodiments of the dual-stage syringe comprise one or more electromagnets, the electromagnets may be activated before the plurality of microspheres are loaded in the dual-stage syringe; the electromagnets may remain activated during storage of the plurality of microspheres to levitate the plurality of microspheres and keep them from settling in the dual-stage syringe; and then the electromagnets may be deactivated after the plurality of microspheres are removed from the dual-stage syringe or after the radioembolization procedure is complete. When the dual-stage syringe comprises multiple electromagnets, these magnetic components may be independently activated or may be activated as a group. In embodiments, the one or more electromagnets may be selectively activated by an electronic interaction, such as by a battery and a switch or other suitable activating means. In some embodiments, the one or more electromagnets may be selectively activated in a manner to create one or more pulsating magnetic fields. In further embodiments, multiple electromagnets may be selectively activated in a manner to create multiple pulsating magnetic fields with varying magnitudes.

In embodiments, the dual-stage syringe may include multiple magnetic components. In further embodiments, the multiple magnetic components may be any combination of permanent magnets, ferromagnetic components, or electromagnets. In one exemplary embodiment, only side walls of the dual-stage syringe may include permanent magnets. In these variations, base wall may include only permanent magnets, only ferromagnetic components, only electromagnets, or a mix of some or all of these elements. In the side walls of the dual-stage syringe may include permanent magnets, and the base wall or a lid may include only electromagnets that may be activated after the plurality of microspheres have been loaded into the dual-stage syringe.

In embodiments, each magnetic component may have any suitable size and shape. For example, each magnetic component may be cylindrical, semi-cylindrical, tube-shaped, box-shaped, planar, spherical, or the like. Generally, the dimensions of the magnetic components may be constrained by size of the dual-stage syringes carrying the magnetic components, which in turn may be constrained by the radioembolization procedure itself. For example, the radioembolization procedure may require a specific dose or delivery device, in which case, the dual-stage syringe may be specifically sized to accommodate said dose or fit within said delivery device. Each magnetic component may have any suitable length. In some embodiments, each magnetic component may have a length of about 5 mm, about 10 mm, about 15 mm, about 20 mm, or each magnetic component may extend along the entire length of one wall of the dual-stage syringe.

Figure 41:
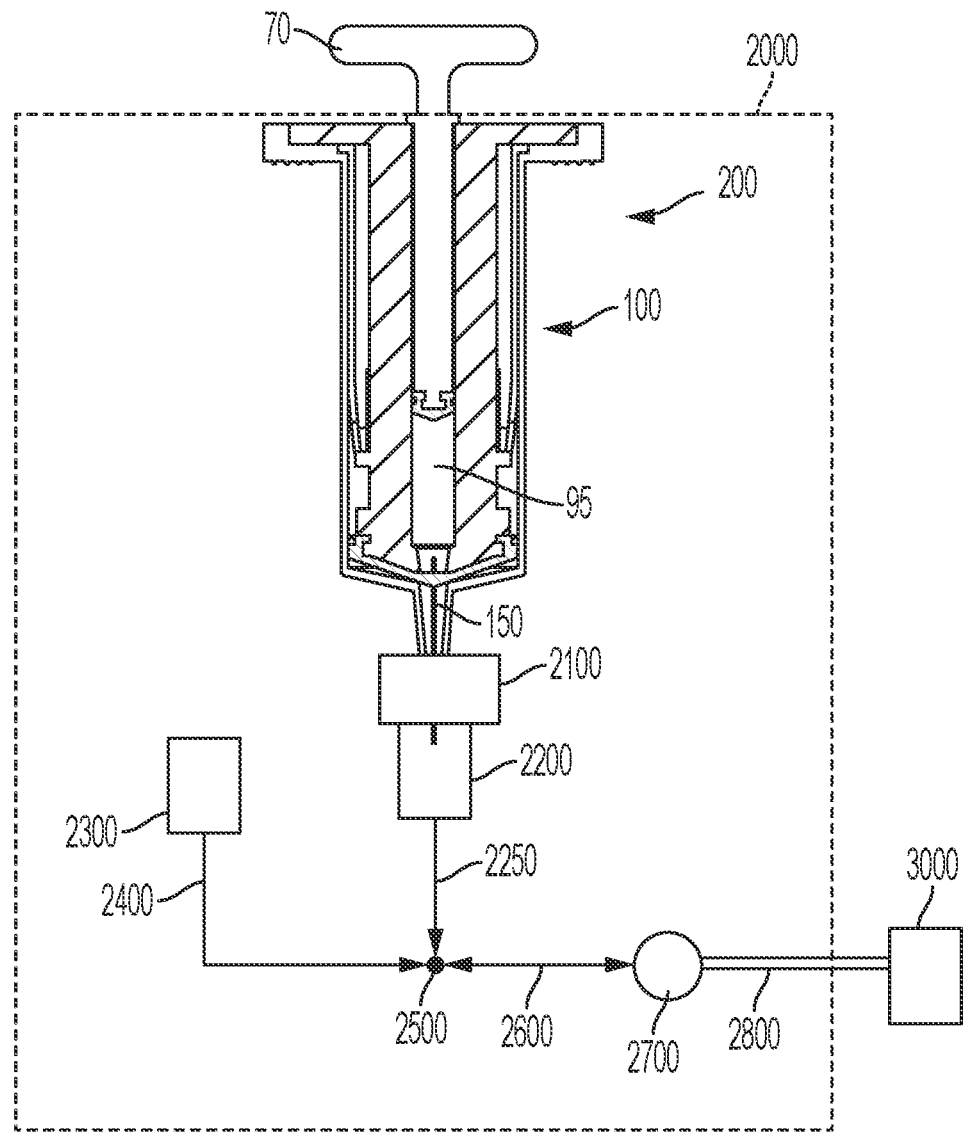
FIG. 41 is a schematic of a sleeved locking dual-stage syringe according to embodiments, incorporated into an example of a radioembolization delivery system for delivery of radioembolization bead solutions to a patient through a delivery catheter in fluidic communication with the sleeved locking dual-stage syringe.

FIG. 41 is a schematic of an exemplary delivery system 2000 into which the sleeved locking dual-stage syringe 200 may be incorporated. Further exemplary delivery systems include those disclosed in U.S. App. Publ. No. 2021/0369946, entitled "RADIOEMBOLIZATION DELIVERY DEVICE," filed concurrently with the present disclosure, which application is incorporated herein by reference in its entirety. In the exemplary delivery system 2000, the sleeved locking dual-stage syringe 200 and additional components may be housed within a system housing, as schematically illustrated in FIG. 40 by dotted lines surrounding the components of the exemplary delivery system 2000. In some embodiments, the sleeved locking dual-stage syringe 200 may include geometry (orientation) features that adapt the sleeved locking dual-stage syringe 200 to be received in the exemplary delivery system 2000. Non-limiting examples of geometry features may include features that orient the sleeved locking dual-stage syringe 200 in the exemplary delivery system 2000 or features that lock the sleeved locking dual-stage syringe 200 in place within the exemplary delivery system 2000

In the exemplary delivery system 2000, the sleeved locking dual-stage syringe 200 is illustrated in the punctured configuration, at which a delivery needle 150 held in place by a needle mount 2100 provides fluidic communication between the system reservoir 2200 and the secondary chamber 95 of the sleeved locking dual-stage syringe 200. One or more additional fluidic reservoirs 2300 (of which, only one is shown in FIG. 41 for illustrative purposes) may be included in the exemplary delivery system 2000 for adding additional fluids to the delivery mixture formed in the sleeved locking dual-stage syringe 200 as previously described. The system reservoir 2200 and the additional fluidic reservoirs 2300 may be fluidically coupled to a mixing valve 2500 through coupling lines 2250, 2400. In turn, the mixing valve may be fluidically coupled to a delivery valve 2700 through an exit line 2600. The delivery valve 2700 may be fluidically coupled to a delivery device 2800 such as a catheter or a microcatheter, for example, which is intravenously fluidically coupled to the patient being treated.

Unless otherwise defined, all technical and scientific terms used herein have the same meaning as commonly understood by one of ordinary skill in the art to which the disclosure belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

As used herein, the terms "horizontal" and "vertical" are relative terms only, are indicative of a general relative orientation only, and do not necessarily indicate perpendicularity. These terms also may be used for convenience to refer to orientations used in the figures, which orientations are used as a matter of convention only and are not intended as characteristic of the devices shown. The present disclosure and the embodiments thereof to be described herein may be used in any desired orientation. Moreover, horizontal and vertical walls need generally only be intersecting walls, and need not be perpendicular.

For the purposes of describing and defining the present disclosure it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A sleeved dual-stage syringe comprising:
   an external barrel having an primary chamber defined through the external barrel from a proximal opening of the external barrel to a distal opening of the external barrel;
   a primary piston having a secondary chamber defined through the primary piston from a proximal opening of the primary piston to a sealed distal end of the primary piston, the primary piston configured to receive a secondary piston through the proximal opening of the primary piston, the secondary piston including, at a secondary piston distal end, a piercing end configured for piercing the sealed distal end of the primary piston; and a locking sleeve disposed within the primary chamber, wherein:

the primary piston and the locking sleeve comprise a locking mechanism configured to define a first boundary, a second boundary distal to the first boundary, and at least three stages, the at least three stages comprising:

an initial stage wherein the primary piston is inserted proximal to the first boundary and is freely movable distally or proximally;

an intermediate stage wherein the primary piston is inserted distal to the first boundary and is prevented from moving proximally beyond the first boundary; and a final stage wherein the primary piston is inserted distal to the second boundary and is prevented from moving proximally beyond the second boundary.

2. The sleeved dual-stage syringe of claim 1, wherein the locking mechanism comprises a body portion having a shape conforming to contours of the external barrel.

3. The sleeved dual-stage syringe of claim 2, wherein the locking mechanism comprises distal catch members.

4. The sleeved dual-stage syringe of claim 3, wherein the distal catch members comprise catches of varying lengths around the circumference of the body portion at the distal end of the body portion.

5. The sleeved dual-stage syringe of claim 3, wherein the distal catch members comprise long catches and short catches alternating around the circumference of the body portion at the distal end of the body portion.

6. The sleeved dual-stage syringe of claim 5, wherein long-catch ends of the long catches, short-catch ends of the short catches, or both are angled inwardly of the sleeved dual-stage syringe.

7. The sleeved dual-stage syringe of claim 5, wherein long-catch ends of the long catches, short-catch ends of the short catches, or both are angled outwardly of the sleeved dual-stage syringe.

8. The sleeved dual-stage syringe of claim 1, wherein the locking mechanism comprises one or more features for integrational assembly.

9. The sleeved dual-stage syringe of claim 8, wherein the locking mechanism comprises a proximal ridge configured to seat the locking mechanism in the proximal opening of the external barrel.

10. The sleeved dual-stage syringe of claim 1, further comprising one or more sensors.

11. The sleeved dual-stage syringe of claim 1, wherein the external barrel further comprises shielding.

* * * * *